(12) United States Patent
Zhang

(10) Patent No.: US 10,016,566 B2
(45) Date of Patent: Jul. 10, 2018

(54) SYSTEMS AND METHODS FOR MAINTAINING BREAST OR UDDER HEALTH

(71) Applicant: Henian Zhang, Atlanta, GA (US)

(72) Inventor: Henian Zhang, Atlanta, GA (US)

(*) Notice: Subject to any disclaimer, the term of this patent is extended or adjusted under 35 U.S.C. 154(b) by 797 days.

(21) Appl. No.: 14/265,770

(22) Filed: Apr. 30, 2014

(65) Prior Publication Data

US 2014/0236072 A1 Aug. 21, 2014

Related U.S. Application Data

(63) Continuation of application No. PCT/US2012/062662, filed on Oct. 31, 2012.

(60) Provisional application No. 61/553,694, filed on Oct. 31, 2011, provisional application No. 61/691,891, filed on Aug. 22, 2012.

(51) Int. Cl.
| | |
|---|---|
| *A61M 37/00* | (2006.01) |
| *A61M 13/00* | (2006.01) |
| *A61M 1/06* | (2006.01) |
| *A61F 7/02* | (2006.01) |
| *A61M 35/00* | (2006.01) |
| *A01J 7/04* | (2006.01) |
| *A61D 7/00* | (2006.01) |
| *A61F 7/00* | (2006.01) |

(52) U.S. Cl.
CPC .............. *A61M 13/003* (2013.01); *A01J 7/04* (2013.01); *A61D 7/00* (2013.01); *A61F 7/02* (2013.01); *A61M 1/06* (2013.01); *A61M 1/062* (2014.02); *A61M 35/00* (2013.01); *A61F 7/007* (2013.01); *A61F 2007/0021* (2013.01); *A61F 2007/0062* (2013.01); *A61M 2202/02* (2013.01); *A61M 2205/3368* (2013.01); *A61M 2205/36* (2013.01); *A61M 2205/362* (2013.01); *A61M 2205/3606* (2013.01); *A61M 2210/1007* (2013.01); *A61M 2250/00* (2013.01)

(58) Field of Classification Search
CPC ........ A61M 1/06; A61M 1/064; A61M 1/066; A61M 2205/3368; A61M 13/003; A61M 1/062
USPC ....................................... 604/23, 73–76, 113
See application file for complete search history.

(56) References Cited

U.S. PATENT DOCUMENTS 6,358,226 B1 * 3/2002 Ryan ..................... A61M 1/062
604/113

* cited by examiner

*Primary Examiner* — Phillip Gray

(57) ABSTRACT

Provided herein are systems and methods for maintaining breast or udder health. The systems include a first container comprising a top and a bottom, one or more cups attached to the top of the container and a first temperature-controlling element for providing vapor from the container to a breast or udder via the cup.

21 Claims, 13 Drawing Sheets

SYSTEMS AND METHODS FOR MAINTAINING BREAST OR UDDER HEALTH

CROSS-REFERENCE TO RELATED APPLICATIONS

This application is a continuation of International Application No. PCT/US2012/062662, filed Oct. 31, 2012, which claims the benefit of U.S. Provisional Application No. 61/553,694, filed Oct. 31, 2011 and which also claims the benefit of U.S. Provisional Application No. 61/691,891, filed Aug. 22, 2012. The foregoing references are hereby incorporated by reference in their entirety.

BACKGROUND

Breasts and udders contain mammary glands. They are subject to a number of diseases and conditions. Some of these diseases include but not limited to abnormal nipple conditions, fibrocystic breast changes, infections and inflammations, and neoplasms.

There are certain diseases and conditions that occur or cause complications mostly during pregnancy and postpartum. For example, sore breasts, breast enlargement, breast engorgement, plugged milk ducts, cracked or bleeding nipples, inverted or flat nipples, fungal infection (e.g., yeast infection or thrush), and breast infection. Breast engorgement is the painful overfilling of breasts with milk caused by an imbalance between milk supply and infant or milking demand. It occurs in the mammary glands due to expansion and pressure by the synthesis and storage of breast milk, which happens when the breast switches from colostrum to mature milk or when breastfeeding or other expression of milk is not sufficiently frequent. Engorged breasts or udders may swell, throb and cause mild to extreme pain. Engorgement may result in a plugged milk ducts and/or infection.

A plug in the milk duct can form when milk becomes static, thickens or dries out. The formation of a plug makes it more difficult to release the milk causing more pain. If left untreated, a plugged duct may become infected, resulting in mastitis or abscess.

Mastitis is a common occurrence among breastfeeding women and among dairy animals. Reduced milk flow, e.g., due to plugged milk ducts, tends to render a subject to be more susceptible to infection. Mastitis is caused by bacteria that enter the breast through small cracks in the nipple or the udder through the teats. Upon entering, bacteria can multiply in the fatty tissue surrounding the milk ducts causing swelling, warmth, or pain. In the most severe infections, an abscess may develop, which needs to be drained by an office procedure or with surgery. The World Health Organization (WHO) estimates that the prevalence globally of mastitis is approximately 10% of breastfeeding women. A US-based study showed that as many as 33% of breastfeeding women developed mastitis (Riordan, J. M., and F. H. Nichols: A descriptive study of lactation mastitis in long-term breast-feeding women. *Journal of Human Lactation*, 6(2):53-58 (1990)). Studies also suggest that women with a history of mastitis have a higher incidence rate of breast cancer (Lambe et al., *Epidemiology* 20(5):747-51 (2009)). Most women that develop breast infections usually do so within the first few weeks after delivery or at the time of weaning. Women with diabetes, chronic illness, AIDS, or an impaired immune system may be more susceptible to the development of mastitis. Symptoms associated with breast infection or mastitis include, but are not limited to, breast enlargement, breast tenderness or warmth to the touch, breast lump and hardened breast, pain or a burning sensation continuously or while breast-feeding, itching, nipple discharge, nipple sensation changes, swelling of the breast, skin redness, and fever.

Women including breastfeeding women are also subject to fungal or yeast infection (thrush) which may cause the woman to feel severe stinging or burning pain on the surface of the nipples or deep inside the breast. The nipples may be itchy and appear puffy, scaly, flaky, weepy, or have tiny blisters. Alternatively, nipples may appear completely normal, but be severely painful.

Conventional treatments for the conditions and diseases described above include placing moist and warm packs at the place of infection over the breast, taking a warm shower before breastfeeding, applying a cold press to reduce pain and swelling, taking antibiotic medications for the infection, and draining of abscesses. For fungal infection, the treatments include rinsing nipples with a solution of water plus an acid such as vinegar after nursing and then air drying; applying antifungal creams; numbing nipples with cold substance such as ice wrapped in washcloth; and taking pain relieving medications.

However, these methods are not convenient or comfortable for most subjects. For example, placing warm moist towel over breasts may introduce more bacteria and rinsing nipples with a solution after every nursing event is not convenient. Taking a warm shower before every breastfeeding is not practical. The antibiotic approach requires a prescription and takes about 24 hours to work. The subject also has to take the medicine for 7 to 10 days before the symptoms are gone and such medications can enter the breast milk and enter the nursing infant or milk supply.

Mastitis can also occur in other mammals such as cows, goats, ewes, does, mares and sows. In fact, mastitis is one of the most significant diseases within the dairy industry. Even on well-managed farms, mastitis can occur in at least 33% of cows. It results in a considerable loss in profitability and, in extreme cases, in death of the dairy cow. Mastitis in dairy animals can occur in either a clinical or subclinical state. Dairy animals that develop clinical or subclinical mastitis are less productive and at greater risk for future mastitis. Symptoms of clinical mastitis include abnormal milk production, swollen udders, and elevated body temperature. Subclinical mastitis is the most common form of mastitis in the dairy industry and detection is only possible through diagnostic or laboratory tests as the milk of dairy animals with subclinical mastitis appears normal. Detection of subclinical mastitis occurs through analysis of milk sample for somatic cell count (SCC) and/or bacteria. Dairy animals are usually considered to have subclinical mastitis when the SCC exceeds about 200,000 cells/ml. Subclinical mastitis has great economic consequence as udder infection results in long term reduction of milk yield. Conventional methods of prevention and treatment of mastitis of dairy animals includes reducing exposure of the dairy animal to the bacteria, enhancing the immune system of the animal, and antibiotics. However, such methods are difficult to implement and/or maintain. For example, antibiotics should be administered to infected animals for about 60 days and milk should be constantly monitored for the presence of elevated SCC and bacteria. Therefore, prevention of initial infection is important to the dairy industry.

SUMMARY

Provided herein are systems and methods for maintaining breast or udder health. Specifically, provided herein are methods and systems for providing certain substance or substances to breasts or udders to prevent and/or treat causes, symptoms, and conditions of breast and/or udder diseases. The systems include a first container comprising a top and a bottom, one or more cups attached to the top of the container, and an optional temperature-control element. The system provides a substance or substances, e.g., vapor, from the container to a breast or udder via the cup. Optionally, the systems comprise a separate reservoir to collect milk or other secretion or discharge from breasts or udders. Optionally, the system comprises multiple containers or compartments that contain one or more different substances.

Further provided is a container with a base and an upper portion, wherein the base is configured for containing a vapor producing substrate and wherein the upper portion is continuous with the base and has one or more angled openings configured for accepting a breast, udder or teat. Optionally the upper portion is detachably connected to the base. Optionally, the angle of the opening is adjustable.

The details of one or more embodiments are set forth in the accompanying drawings and the description below. Other features, objects, and advantages will be apparent from the description and drawings, and from the claims.

DETAILED DESCRIPTION

Figure 1:
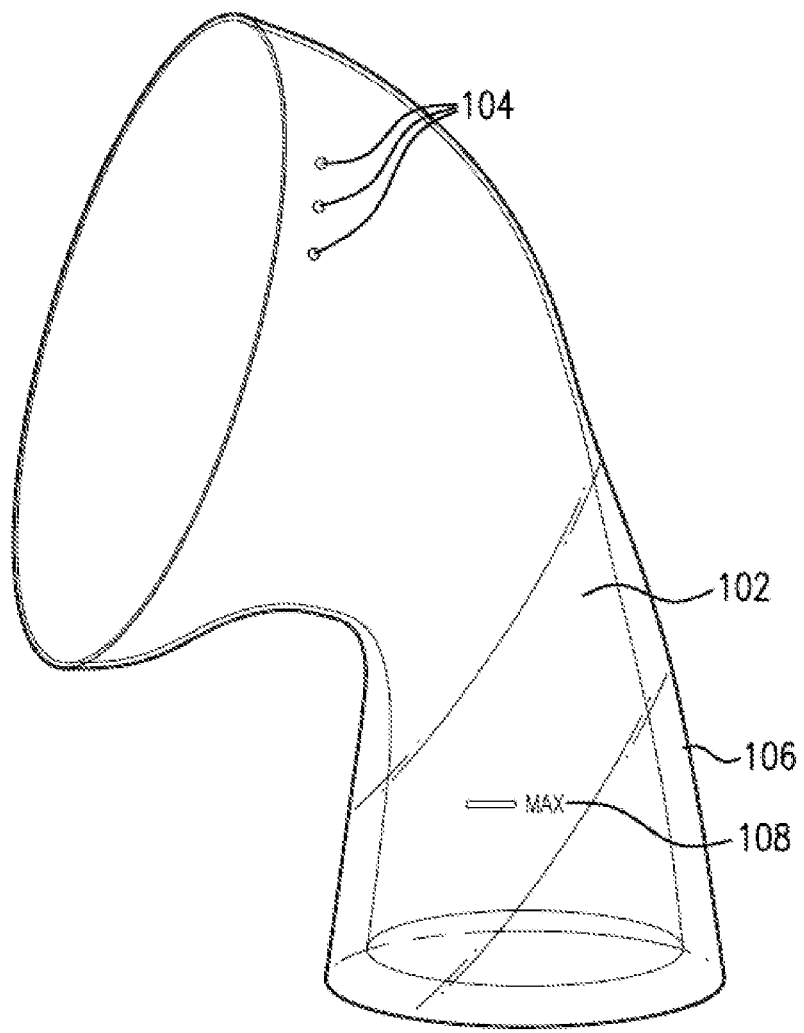
FIG. 1 is a schematic of an exemplary system for maintaining breast health provided herein.

Provided herein are methods and systems for maintaining and improving breast health. For example, the present disclosure provides methods and systems for providing a substance or substances to breast or udder to prevent and treat causes, symptoms, and conditions of breast and/or udder diseases. The substance includes but not limited to vapor, gas, particles, or a mixture of any combination of vapor, gas, and particles. For example, the present disclosure provides methods and systems to prepare breasts for breastfeeding or pumping (e.g., to extract milk), to soothe breasts during and/or after breastfeeding or pumping, to prevent or reduce one or more symptoms associated with sore breasts, breast engorgement, breast infection (e.g., bacterial or fungal), mastitis, nipple injuries, nipple discharge, or other diseases or conditions resulting in painful or discomfort to breasts or udders. Similarly, also provided are methods and systems to prepare udders for milking, to soothe udders during and/or after milking, to prevent or reduce one or more symptoms associated with clinical or subclinical udder diseases and conditions such as mastitis. As used herein the term milking includes the pumping of udders to extract milk.

The provided methods and systems provide vapor, particles or a mixture of any combination of vapor, gas, and particles (optionally, temperature-controlled) to one or both breasts or to the udder of a subject. Optionally, the vapor or mixture has a high temperature, which helps open milk ducts, warms breasts or udders and aids milk or other secretion and discharge flow from the nipple(s) or teat(s) naturally. Warm vapor or mixture can increase the blood circulation. Warm vapor can also help open plugged milk ducts and provide pain relief from engorgement or infection. Optionally, the vapor or mixture has low temperature, which can reduce swelling and provide pain relief from engorgement or infection. The provided methods and systems provide a more convenient way of maintaining breast or udder health. Applying warm vapor to one or more breasts or udders before or during breastfeeding or pumping, helps open the milk ducts and increases the ease by which milk flows naturally from the nipple or teat. This protects the nipples or teats from injury, e.g., cracking, and pain, and prevents development of infection. Applying the provided methods and systems upon early signs of infection (e.g., at a subclinical stage) increases the speed of curing or preventing the infection and/or limits the severity of the infection. The vapor or a mixture can optionally include, antiseptics, germicides, antibiotics, skin conditioning agents, skin protectants, and the like. Long term use can lead to healthier breasts and udders and a more comfortable breastfeeding/pumping experience. It can also extend the breastfeeding or milking period as mastitis is the leading cause of unplanned termination of breastfeeding or milking.

The provided systems can be adopted and configured into many forms including but not limited to hand-held, stand-alone, to be contoured to fit breast/udder and inserted into a supporting substrate such as bra, or to be integrated into or as an attachment for a breast pump, a milking machine or any other devices.

Provided herein are systems for maintaining breast or udder health. The systems include a first container comprising a top and a bottom. The system optionally includes a first removable substrate covering the top of the container, the removable substrate comprising a top surface and a bottom surface, and a first cup attached to the top surface of the substrate. The system optionally includes a first temperature-controlling element for providing temperature-controlled substance from the container to the cup. Optionally, the removable substrate comprises a first and second cup attached to the top surface of the substrate and substance (optionally, temperature-controlled) is provided to one or both of the cups. More than two cups can be used for dairy animals. For example, the system can comprise one cup per teat of an udder of a dairy animal. Optionally, the system comprises four cups. Optionally, one cup covers an entire udder.

By way of example, provided is a container with a base and an upper portion, wherein the base is configured for containing a vapor and/or gas producing substance and wherein the upper portion is continuous with the base and has one or more angled openings configured for accepting one or more breasts, udder or teats. Vapor and/or gas released by the substance in the container is guided into the openings to reach breast and udder. Optionally, the angled opening is on a cup that is open to the base. The cup can be connected to the base through a connector. The connector can comprise a rotatable coupling or flexible member, which is optionally variable in angle in reference to the base. Thus, the upper portion is optionally detachably connected to the base and the angle of the opening or the cup is optionally adjustable.

By way of another example, provided is a system for maintaining breast or udder health comprising a container comprising a top and a bottom, an optional removable substrate covering the top of the container, the removable substrate comprising a top surface and a bottom surface, one or more cups attached to the top surface of the substrate, and a temperature-controlling element for providing temperature-controlled substance from the container to one or more cups.

By way of another example, provided is a system for maintaining breast or udder health comprising a first and second container, each container comprising a top and bottom, a first and second removable substrate, covering the first and second containers, respectively, the first and second removable substrates comprising top and bottom surfaces, and first and second cups attached to the first and second removable substrates, respectively. Optionally, the first and second containers comprise a connecting element. Optionally, the connecting element connecting the first and second containers is an adjustable arm to control the distance between the first and second cups. Optionally, in the provided systems, the first and/or second container comprises a handle.

Optionally, the provided system comprises a vapor producing element. The vapor can be produced by many methods including but not limited to evaporation, heating, and mechanical oscillation. By way of example, the system can comprise a heating/cooling element, which can be the same or separate elements for producing the vapor. For example, the system can comprise a capillary force vaporizer or an ultrasonic vaporizer to produce the vapor. For another example, the system can comprise a fan or pump that generates and distribute the vapor.

Optionally, the provided system comprises one or more compartments that stores different substances such as gas, solid and liquid. Optionally, the compartments can be detachably released from the system.

Optionally, the provided system comprises, produces, and delivers the vapor, gas, or particles toward the breast/udder area. The particles can be either solid or liquid or both. For example, the system can include a spray pump. Particles, gases with or without vapor can be sprayed toward the breasts. For example, a substance can be dispensed from a pressurized container as an aerosol.

Optionally, the provided system comprises a collection container. Milk, colostrums and other secretion or discharge from the breast can be collected into the container for use or examination. The container may also serve as a splashguard. When the system tilts, substance in the container will first go into the collector instead of pouring out into the cup and toward the user. Optionally, the collector can be tilted outwards or detachably removable from the system for easy extracting the substance within. Optionally, the collector may have an outlet with a plug in the bottom to drain the substance inside. Optionally, the collector is insulated to maintain its original temperature and is not affected by other elements such as the heating/cooling elements.

Optionally, the provided systems comprise an anti-spill device or baffle system to prevent water or media from coming out of the container. For example, the system may comprise a mesh or screen with holes or other permeable or semi-permeable material, e.g., foam or membrane, which allows release of the vapor but not the water or media. By way of another example, the system may comprise a check-valve, and/or a splash guard. Optionally, the substance can be directed to a separate substrate acting as an anti-splash system which is located on the way between the medium container and the cup. Optionally, the separate substrate comprises absorbent material that absorbs the splashed medium. Optionally, the separate substrate is a container that directs the substance into it instead of going toward the cup and the user. Optionally, the separate substrate is a collection container that also collects milk, colostrum, or other secretion and discharge from the breast.

Optionally, a permeable or semi-permeable layer is present between the base and the opening or cup, wherein the permeable layer comprises one or more perforations designed to allow vapor to reach the opening. The layer also serves as a barrier to prevent and/or reduce liquid from escaping the container.

Optionally, the provided systems comprise a temperature-controlling elements include, but are not limited to, heating elements and cooling elements. Optionally, the system comprises one or more temperature-controlling elements; for example, a heating element and a cooling element for providing temperature-controlled vapor from the container to the cups. If the removable substrate comprises two or more cups, the cooling element optionally can be used to provide cool vapor to one cup while the heating element can be used to provide warm vapor to the another cup. Alternatively, cool vapor or warm vapor can be provided to multiple cups as needed or desired. Heating elements for use in the provided systems include, but are not limited to electric heating devices, resistive foil heating devices, heating wires, solar heating devices, induction heating devices, capillary force heating devices, and ceramic heating devices. By way of example, the heating element can be an electric heating device that heats the substance in the container to a specified degree or range of degrees to provide consistent vapor release. Optionally, the system comprises a heat sink to absorb excess heat from the heating element to provide vapor of the desired temperature. Cooling elements suitable for use in the provided systems include, but are not limited to electric cooling devices, ceramic cooling devices, air cooling devices, heat absorption devices, and refrigeration devices. Optionally, the system comprises a heating/cooling device such as a Peltier device that heats or cools the substance as needed or desired.

Optionally, the temperature controlling element can be an element separate from the system. For example, the system may comprise a base that has an engageable element that engages with the heating/cooling element to provide a heating/cooling source to the substance in the system.

Optionally, the system comprises an insulation material or layer. Insulating materials generally surround the heating/cooling element and/or the container to reduce heat loss. Optionally, the insulation material includes heat reflecting material to additionally redirect otherwise escaping heat back into the substance reservoir. The insulating material or layer also keeps the outside of the device cool to the touch both increasing comfort and lowering the chance of injury to the user or subject. For example, the insulating material can be a foam.

Optionally, the provided system comprises a double-wall. For example, the container and/or the heating/cooling element can comprise an outer wall and an inner wall and a space between the outer wall and inner wall. Optionally, the space between the inner and outer walls is filled with an insulation material, e.g., foam. Optionally, the space between the inner and outer walls is filled with a medium, e.g., a liquid, at a lower temperature than the temperature of the medium inside the container to serve as a heat barrier for the user when touching the container. Similarly, the space can be filled with a medium of a higher temperature than the temperature of the medium inside the container to serve as a cold barrier for the use when touching the container. Optionally, the system comprises a vacuum to remove heat from the system, e.g., the heating element. Optionally, the space between the inner and outer wall is vacuumed.

Optionally, the provided system contains an ionizer.

Optionally, the provided system contains an element that helps control and change particle size that applied on the breasts/udder. For example, the element can be a filter that only allows particles with certain size to go through. By way of example, the element can be pressurized dispenser for releasing gas, liquid, solid particles.

Optionally, the provided system is made with a complete or partly transparent material to indicate the volume of the substance within. Optionally, indicator lines can be painted inside or outside of the container.

By way of an example, the provided a system for maintaining breast health comprises a container with a top portion and a bottom portion forming a first cup with a base, wherein the top portion comprises an expanded opening configured for surrounding a breast or udder, wherein the opening is on a plane at an angle with the base of the bottom, wherein the angle of the opening is equal to or less than about 90 degrees and equal to or more than about 15 degrees as compared to the base of the bottom. The container is configured for holding a vapor producing substance or a heating element as described herein. The top portion optionally comprises one or more second openings on an upper surface of the top portion. Optionally, the bottom portion comprises a second container for collecting milk from a breast or udder.

Optionally, the system comprises a material suitable for heating and cooling. For example, the system can be placed in a microwave or heating or a refrigerator or freezer for cooling.

Also provided is a system for maintaining breast health comprising a first container comprising a top and a bottom. The top part is configured for surrounding the breast or udder region of the subjects. The curvature of the container allows vapor to flow to the top part of the container, which comprises small openings to balance the pressure. Optionally, the system comprises an inner pocket to hold the milk leaked from breasts or udders.

Any of the systems for maintaining breast health as described herein can be configured for integration into or as an attachment for a breast pump or milking machine. For example, the system optionally comprises a first container comprising a top portion and a bottom portion, a first removable substrate covering the top of the container, the removable substrate comprising a top surface and a bottom surface, a first cup attached to the top surface of the substrate, a first connector between the cup and the top portion of the first container; and a second connector for attachment to a breast pump or milking machine.

Optionally, the system comprises a pumping system. The temperature controlling element heats or cools the vapor and other substances in a small chamber within the container. The vapor and/or other substance is then pumped out to the cups.

The temperature of the vapor can be controlled using a temperature control unit, e.g., a knob or electronic control panel that allows the user to set the desired temperature of the vapor or substance in the container. The temperature control unit is in communication with the temperature-controlling element or elements (e.g., the heating and/or cooling elements) to control the temperature of the vapor that passes from the container to the cup or cups.

Instead of heating and cooling elements, the containers of the provided systems may contain a solid (e.g., ice) or liquid (e.g., water) soothing medium of a selected temperature. Optionally, the solids or liquids are provided to the containers in a receptacle containing the solid or liquid. In this system, the user or subject selects the temperature by selecting the temperature of the fluid or solid. For example, water can be heated externally to the system to a desired temperature and then provided to the container, e.g., in a receptacle for use. Optionally, the system comprises a material suitable for heating and cooling. Thus, the system can be placed in a microwave for heating or a refrigerator or freezer for cooling. For example, the system and/or the substance within can be microwaved or frozen.

By way of another example, the provided system can be made into a cup shape so that the inner side of the cup fits the breasts and udder. For example, the provided system can be put into a bra or bra-ike element. Exemplary bra-like breast pumps are known and are described in U.S. Pat. No. 8,142,393, which is incorporated by reference in its entirety. The system can be configured for surrounding the breast or udder region of the subjects. The system, optionally, further comprises a pad. Optionally, the pad is removable and/or disposable. Optionally, the pad is made with reusable material such as a dishwasher- and/or washer-safe material for repeated use. Optionally, the pad can comprise several layers. For example, the top layer can be made of soft, absorbent or permeable material that is suitable to contact skin. A second layer can be made of material that contains soothing media such as gel, water, oil, and/or medication. Vapor can be released upon heating or cooling of the pad. The system optionally comprises a power supply. Optionally, the system comprises a temperature controlling element. The outside of the system can comprise an insulation layer to maintain temperature within, conserve energy and protect the user. Optionally, the pad can be heated or cooled prior to insertion into the system. In one embodiment, the system does not contain a power supply or heating element and the pads, which can be removable, reusable or disposable, can be heated (e.g., by microwave) or cooled (e.g., by freezing or refrigeration) prior to use. The pads can contain a solid such as ice or a liquid such as water and/or other agents including oils or medications. The pads may comprise several layers. For example, the pad may have a top layer which is comfortable skin allergy tested, a middle layer that is absorbent, and a bottom layer that is heat resistant and liquid proof.

Optionally, the provided systems comprise a power supply. DC power, AC power, a battery, a number of batteries, a rechargeable battery, or any combinations thereof, may power the provided systems. Optionally, the system is solar powered. One skilled in the art will appreciate that any means or way of delivering power to the provided systems can be used.

Optionally, the provided systems comprise a volume control element that controls the amount of vapor or gas that passes from the container or vaporizer to the cup. For example, in the provided systems, the removable substrate comprises one or more openings that extend from the top surface of the substrate to the bottom surface of the substrate to allow vapor (optionally temperature-controlled) to pass from the container to the cup. By way of example, the removable substrate comprises one opening per cup, the cup located or attached to the substrate above the opening. Optionally, a valve is located in or above the opening to control the amount of vapor that passes from the container to the cup. The valve optionally comprises a vapor or gas control switch capable of opening and closing the valve to control the amount of vapor or gas that passes from the container to the cup. Suitable valves for use in the provided systems include shutter-like apparatuses that open and close based on manipulation of the vapor control switch. The shutter-like apparatus can contain multiple blades or units that move to provide an opening of desired size based on manipulation of the vapor control switch. Optionally, the removable substrate comprises a fixed plate located between the cup and the openings, the fixed plate comprising one or more holes to allow temperature-controlled vapor to pass from the container to the cup. Optionally, the removable substrate comprises a movable plate located between the cup and the openings, the movable plate comprising one or more holes and a vapor flow control switch to control the amount of vapor that passes from the container to the cup. By way of example, the provided system can comprise a movable plate and a fixed plate located between the opening in the substrate and the cup. The movable plate and fixed plate can comprise holes of the same number and/or the same size. The movable plate can be located between the fixed plate and the cup or the movable plate can be located between the fixed plate and the opening. Optionally, the vapor flow control switch facilitates movement of the movable plate. Flow of vapor is controlled by moving the movable plate using the vapor flow control switch such that the holes in the fixed plate partially or completely overlap the holes on the movable plate. Optionally, the movable plate can be moved such that none of the holes in the movable plate overlap with the holes in the fixed plate to prevent vapor from flowing from the container to the cup.

Figure 3:
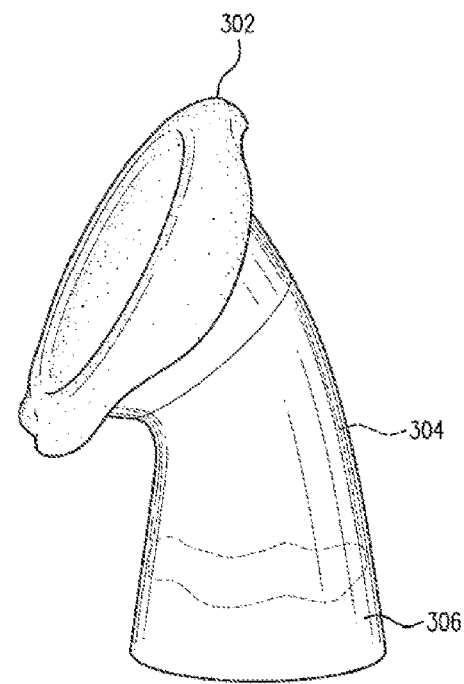
FIG. 3 is a schematic of an exemplary system for maintaining breast health provided herein with a cup made of foldable material.
Figure 13:
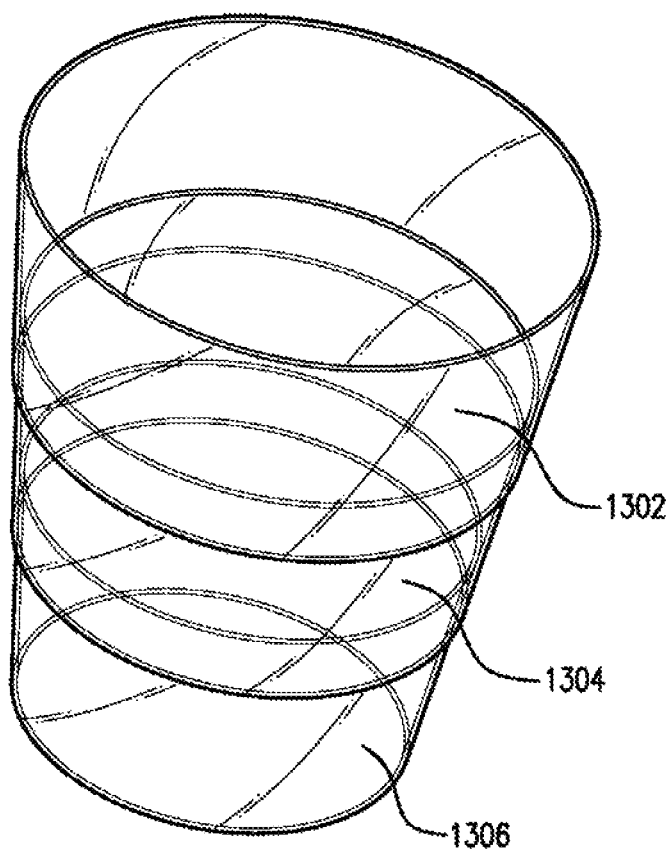
FIG. 13 is a schematic of a collapsible cup for use in the provided systems for maintaining breast health.

The cups of the provided systems are optionally detachable or removable from the substrates. Optionally, the cups are made with transparent or semi-transparent material. Optionally, the cups comprise one or more holes or small openings to balance the pressure and promote air flow. The cups can be configured to direct milk or other breast secretions released from the breast or udder to flow into a collection container. The size of the cups is optionally adjustable or replaceable cups of various sizes can be provided and used based on the size of the breast or udder. The size of the cups can be adjusted, e.g., increased or decreased, based on the addition or removal of one or more extension rings to the cups. By way of another example, the size of the cups can be adjusted by collapsing or expanding the cup, e.g., as shown in FIG. 13. Optionally, the cup is made of a flexible material that is foldable or bendable inward and/or outward to form cups of different diameters, for example, as shown in FIG. 3. Optionally, the flexible cup can be folded into the flexible member and/or container for easy storage. Alternatively, the system can comprise one or more of a variety of cup sizes corresponding to various standard bra cup sizes, e.g., A, B, C, D, and the like. The cups, flexible members, and/or containers of the provided systems are optionally made of a dishwasher safe material for sterilization and repeated use. Optionally, the cups, flexible members and/or containers are made of a microwave-safe material and/or refrigeration/freezer safe material for heating or cooling the soothing medium. The portion of the cup that comes in contact with skin should be constructed of a safe and comfortable material and should not cause skin irritation.

Optionally in the provided systems, the angle of the cups and/or the distance between the cups is adjustable. For example, each cup can be attached to the substrate with a flexible member that allows the cup to be moved in any direction. Optionally, the cups are connected to the container through a connector (e.g., tube). The connector can be of any suitable length. Thus, provided is a system for maintaining breast health comprising a first container comprising a top and a bottom, a first removable substrate covering the top of the container, the removable substrate comprising a top surface and a bottom surface, a first cup attached to the top surface of the substrate, a connector with various lengths that connects the cup with the container, and a heating and/or cooling element for providing temperature-controlled vapor from the container through the connector to the cup.

The containers of the provided systems can be made of any suitable material including dish-washer, microwave, and/or refrigerator/freezer safe materials. Optionally, the containers comprise a liquid and the container further comprises a stirring apparatus. Stirring apparatuses include, but are not limited to, bars, e.g., magnetic stir bars, paddles or rods. The stirring apparatus may be powered by hand pressure through a small rotor controlled by a switch, handle or button. Optionally, the stirring apparatus is controlled by the power source of the system.

Optionally, the containers further comprise one or more vaporizing elements (e.g., fans or pumps) to generate and/or assist in the dispersion of the vapors. Optionally, the vaporizing element is a capillary vaporizing system, for example, as described in U.S. Publication No. 2010/0142934, which is incorporated by reference herein in its entirety. Optionally, the vaporizer is an ultrasonic vaporizer. Optionally, the container comprises an aerosolizing device. Optionally, the system comprises a pumping system that heats or cools the vapor or liquid in a small chamber within the container. The vapor and/or small liquid particles is then pumped out to the cups. Optionally, the system comprises a pump, such as an air pump, that pumps the vapor from the container to the cup.

Optionally, the system comprises a spray pump to spray fine particles (vapor, liquid, or solid) towards the breasts or udders. The spray pump may include separate containers for storage of different substances. For example, the spray pump may spray fine particles or vapor from an antiseptic, germicidal solution, an essential oil, a skin conditioning agent, a skin protectant, an antiseptic, an antibiotic, or combinations thereof.

Optionally, the containers include a transparent or translucent material through which the medium inside the container can be visualized. For example, the container comprises a liquid and an indicator of liquid level. The indicator is, optionally, a window through which the level of liquid is visible.

Optionally, the provided systems comprise a temperature indicator that displays the actual temperature or information related to the actual temperature. For example, the provided systems can include a thermometer. Optionally, the systems include a digital display panel that shows the actual temperature of the liquid, vapor or solid. For example, the system may comprise a part made with color changing material to indicate the temperature of the media. For example, the color changing material may change to red color when media is hot to give warning to the user.

Optionally, the provided system can automatically turn on or off when a desired temperature has been reached. The provided system can also turn off when warning signs such as low medium level, overheating, and prolonged use of the device occur to enhance the safety.

Optionally, the provided system can comprise a timer. Optionally, the provided system can automatically turn off after passing certain time limit.

Figure 11:
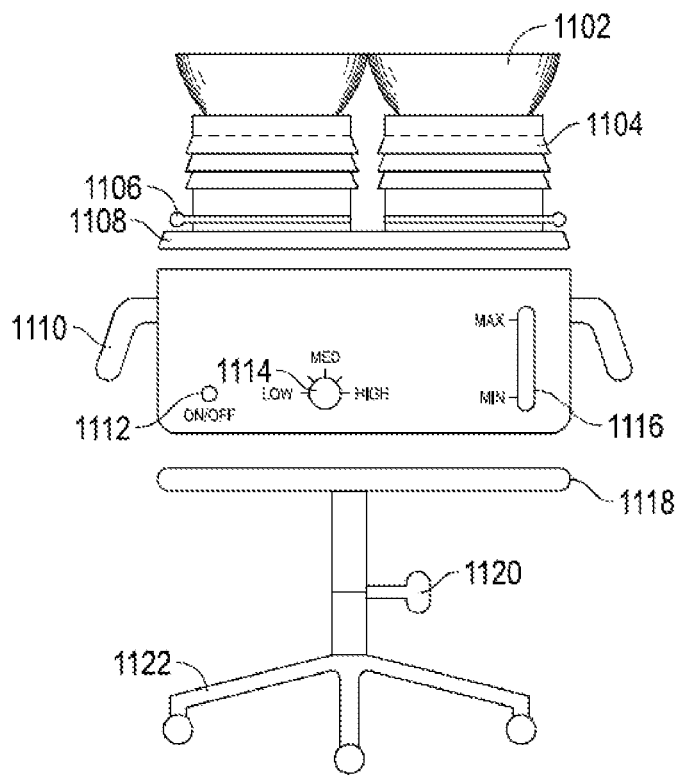
FIG. 11 is a schematic of an exemplary portable, handheld system and base for maintaining breast health provided herein.

Optionally, the provided systems further comprise a platform, the container being mounted on top of the platform. Optionally, the platform comprises an assembly to adjust the height of the platform. Optionally, the platform is mobile. An exemplary system comprising a platform is shown in FIG. 11. It comprises a flat platform 1118 on top, upon which the provided systems can be mounted. It optionally comprises a wheel base 1122 that allows the system and platform on top to move freely. The height is adjustable, for example, by knob 1120.

Turning to the figures, FIG. 1 shows an exemplary system provided herein comprising a container 102 with holes 104 and a base with an insulation layer 106 and a substance level indicator 108.

Figure 2:
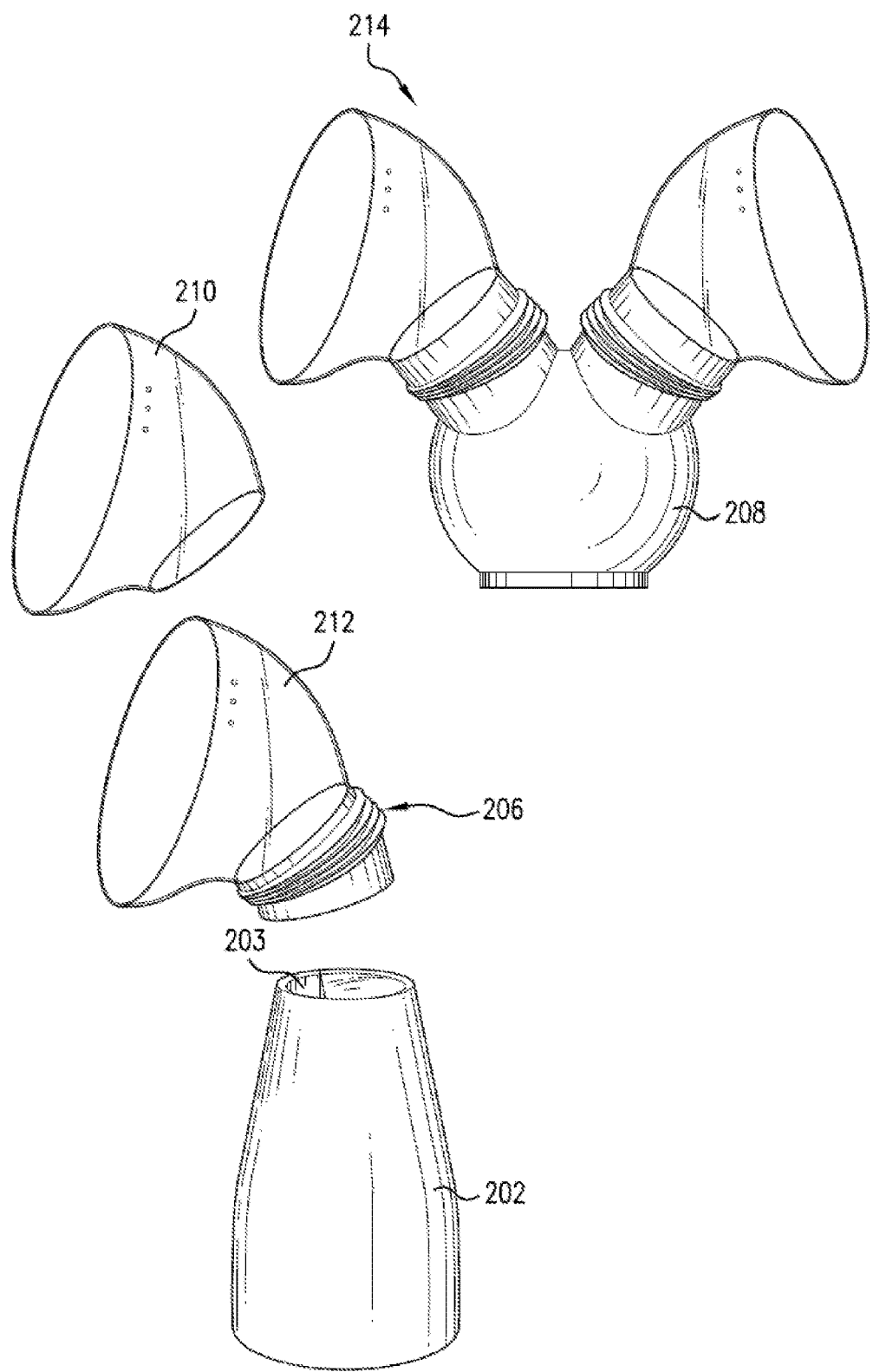
FIG. 2 is a schematic of an exemplary system for maintaining breast health provided herein with three types of removable substrates.

FIG. 2 shows an exemplary system for maintaining breast health provided herein comprising a container 202 with three types of removable substrates. The first removable substrate 210 having a cup with holes, the second removable substrate 212 having one cup with flexible member 206 for adjusting the angle of the cup, the third removable substrate 214 having two cups with flexible members extending from 208 to the cups. The shape of 208 is designed to increase the surface area to maximize the size of flexible members. The container 202 optionally includes a collection container 203 for collecting milk, colostrum or other secretion and discharge. If the system is positioned or tilted toward the user, the substance in the container 202 will flow into the collection container 203 instead of flowing into the cup toward the user. Thus, the collection container 203 can be an anti-spill element. The removable substrates are, optionally, configured to direct the milk or secretion into the collection container.

FIG. 3 is a schematic of an exemplary system for maintaining breast health provided herein with a container 306 and a cup 302 made of a flexible material with an insertable end that can be folded into the container 306 as shown by the dotted lines 304. The cup 302 can be folded outward to fit breasts of different sizes.

Figure 4:
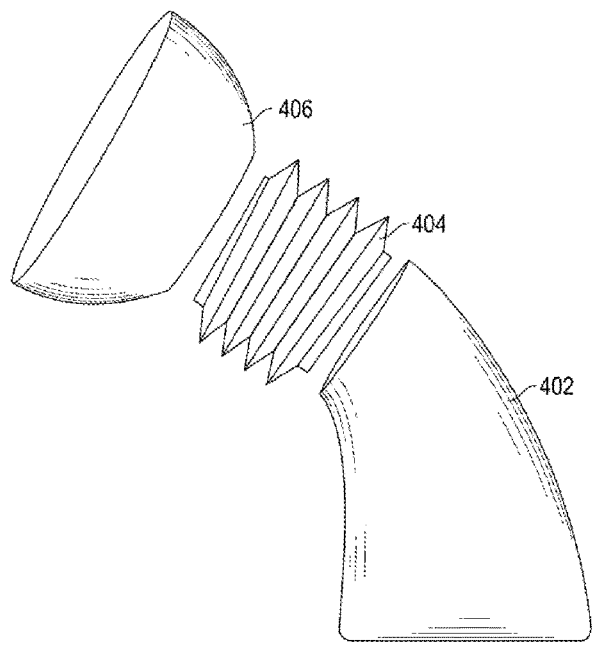
FIG. 4 is a schematic of an exemplary system for maintaining breast health provided herein with a flexible member joining the cup and container.

FIG. 4 is a schematic of an exemplary system for maintaining breast health provided herein with a flexible member 404 joining the cup 406 and container base 402.

Figure 5:
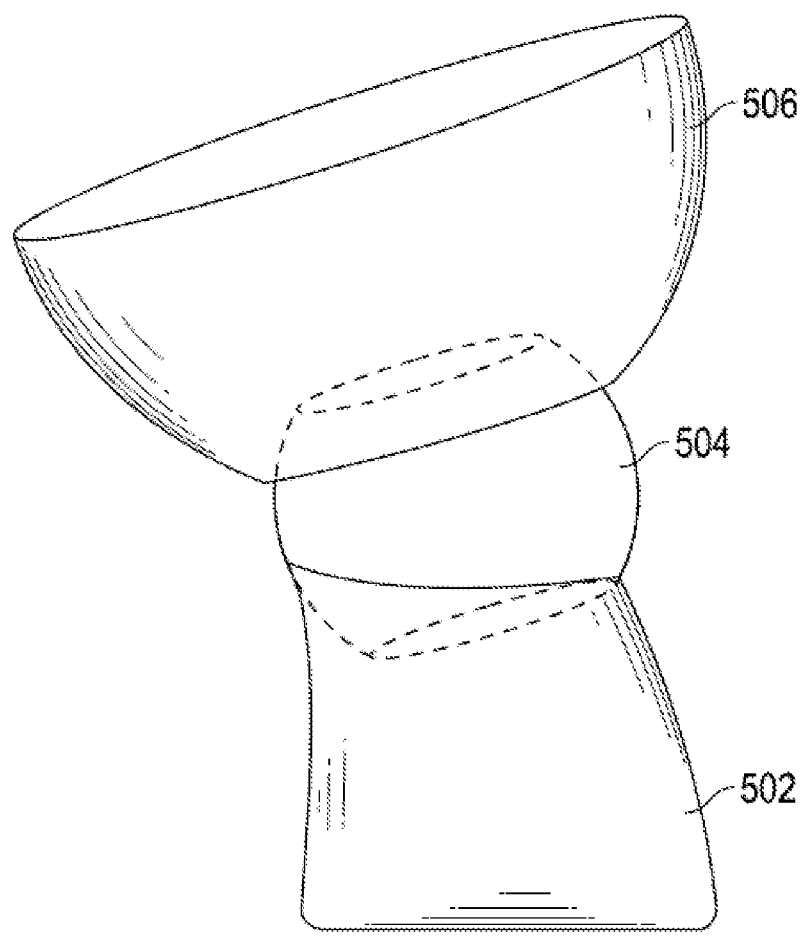
FIG. 5 is a schematic of an exemplary system for maintaining breast health provided herein with a spherical flexible member joining the cup and container.

FIG. 5 is a schematic of an exemplary system for maintaining breast health provided herein with a connector as a spherical flexible member 504 joining the cup 506 and container 502.

Figure 6:
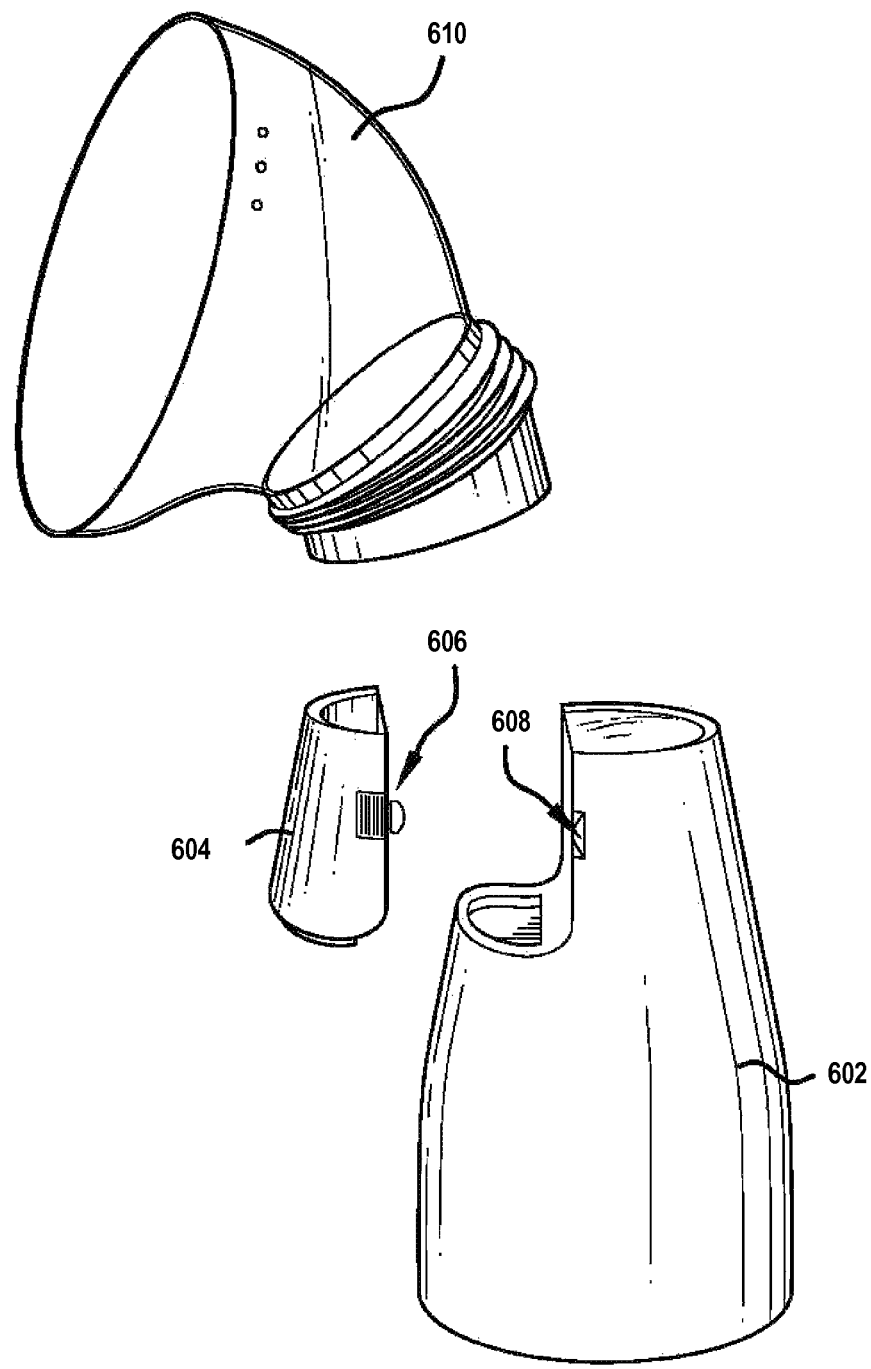
FIG. 6 is a schematic of an exemplary system for maintaining breast health provided herein with a collection container.

FIG. 6 is a schematic of an exemplary system for maintaining breast health provided herein with a collection container 604 for collecting milk, colostrums or other secretion or discharge within the main container 602, which is used to store the substance or substances (e.g., vapor) delivered to the breast. The cup 610 is configured to direct the milk, colostrums or other secretion or discharge into the collection container. Optionally, the collection container 604 is removable or partly detachable from the container 602. This can be achieved by elements 606 and 608. Element 606 is insertable into and removable from element 608.

Figure 7:
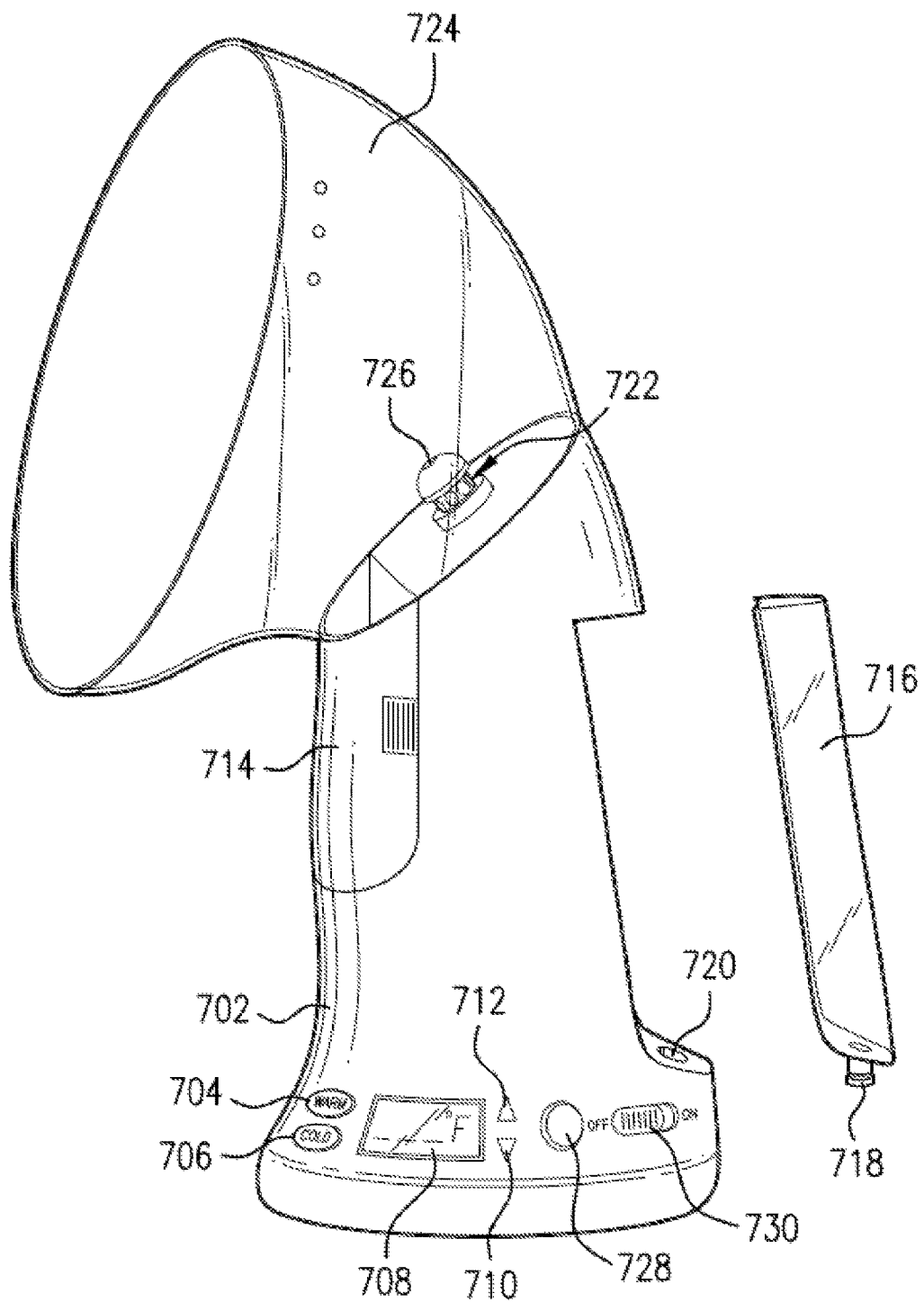
FIG. 7 is a schematic of an electric version of an exemplary system for maintaining breast health provided herein.

FIG. 7 is a schematic of an electric version of an exemplary system for maintaining breast health provided herein including a main body 702 and a cup 724. Optionally, the cup is removable. Optionally, a double cup design such as 214 shown in FIG. 2 can be used instead of the single cup 724. The system contains a removable container 716 that can be filled in substances such as liquids, solids or gases. Substances pass from the container 716 through an outlet 718 and into the main body through an inlet 720. Optionally, the removable container is disposable. The main body optionally contains multiple containers that hold different substances. For example, the main body further comprises a collection container 714 for collecting milk or other secretion and discharges. Optionally, the collection container is removable. The system includes a display panel 708 for displaying temperature, time or other desired properties, a button 704 for selecting warm therapy, a button 706 for selecting cool therapy, a pair of buttons 710 and 712 to adjust temperature, time, substance release speed, or other desired properties, and an on/off switch 730. Substances are released toward the breast/udder through nozzle 722. The nozzle can have multiple sets of openings. For example, a first set of openings are located around the nozzle, which can be used to release vapors, gases, fine liquids or solid particles. The second set of openings are located on top of the nozzle 726, which can be used to release the same or different vapors, gases, fine liquids or solid particles. Substances released from different openings may have different temperatures. The system optionally can spray substances through the nozzle by pressing a button 728.

Figure 8:
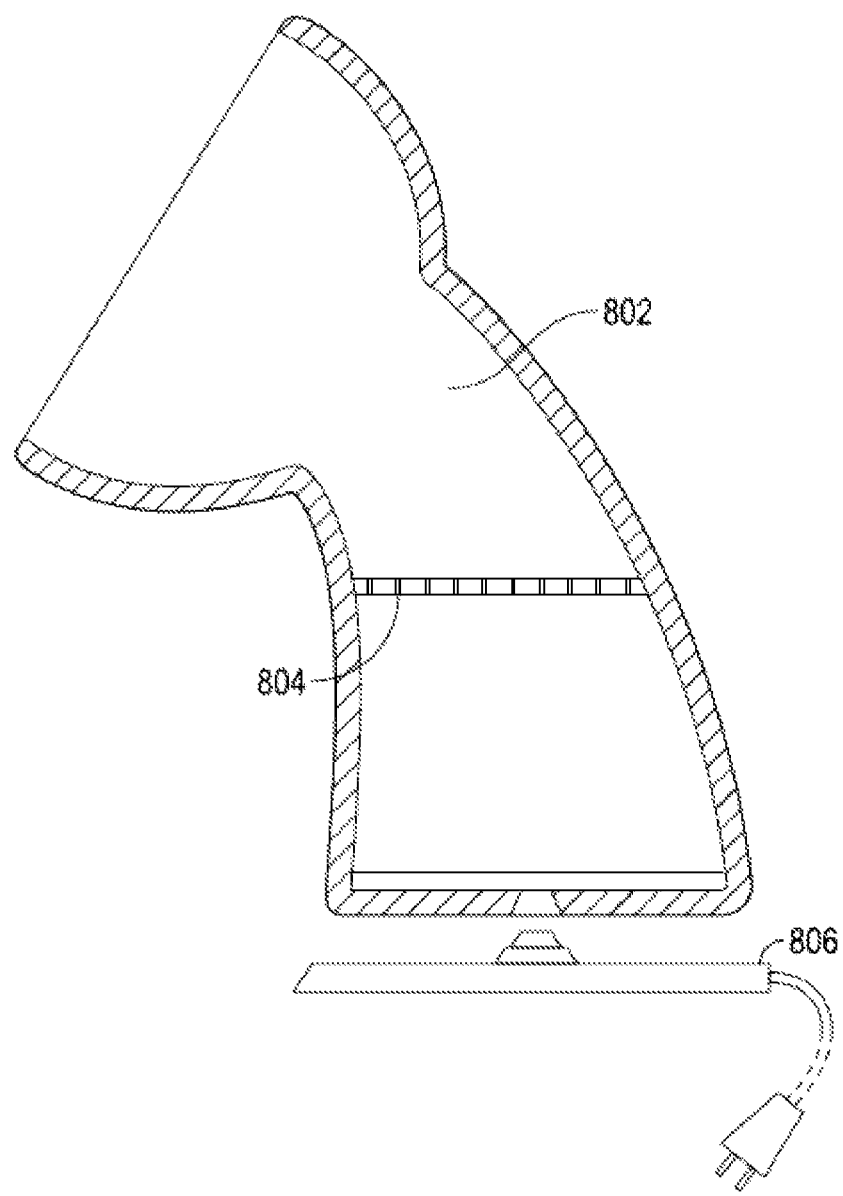
FIG. 8 is a cross-sectional view of an electric version of an exemplary system for maintaining breast health provided herein with an anti-spill element.

FIG. 8 is a cross-sectional view of an electric version of an exemplary system for maintaining breast health provided herein with a permeable layer 804 beneath the cup 802 and a separate heating or cooling element 806 capable of being engaged or separated from the cup and container base.

Figure 9:
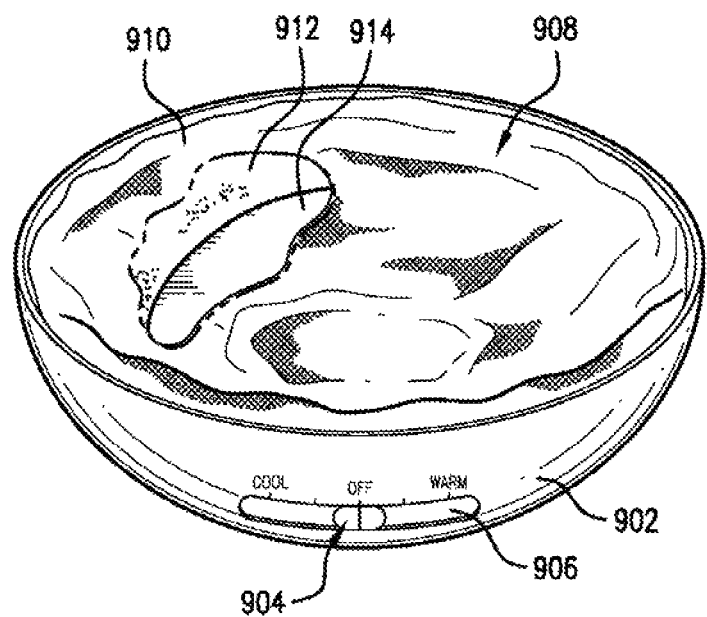
FIG. 9 is a schematic of an electronic version of an exemplary system for bra insertion for maintaining breast health provided herein.

FIG. 9 is a schematic of an electronic version of an exemplary system for maintaining breast health provided herein including a cup 902, a pad 908, a control element 906 consisting of a sliding bar 904 for controlling temperature and power to the system. The system is configured to fit the breast inside a bra. Optionally, the cup and pad can be completely or partly made with flexible material for comfortable fitting. The pad can comprise multiple layers. For example, the pad can include a top layer 910 made with material suitable for contacting skin, a second layer 912 made with absorbent and permeable material that can hold solid or liquid substances, and a bottom layer 914 that is leak proof and is safe to use when temperature varies.

Figure 10:
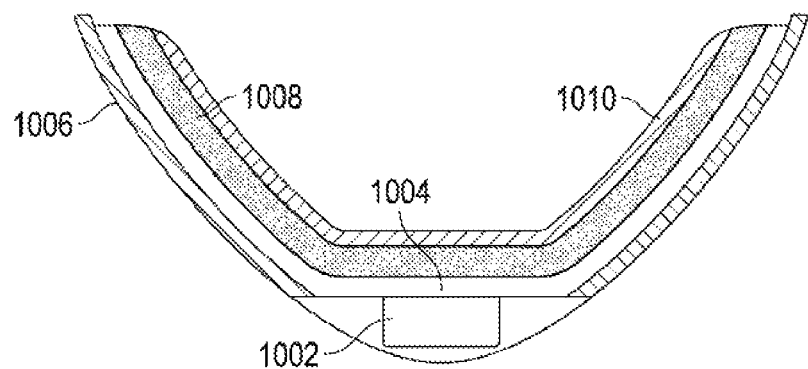
FIG. 10 is a cross-sectional view of an exemplary system for bra insertion for maintaining breast health provided herein.

FIG. 10 is a cross-sectional view of an exemplary system for bra insertion for maintaining breast health provided herein including a power supply 1002, a temperature-controlling element 1004, an insulation layer 1006, a pad 1008 with a soft material layer 1010 for proximation to a breast within the cup. Optionally, the pad is removable. Optionally, the pad can be made of an absorbent or permeable material. Soothing media such as water, oil, and/or medication can be added to the pad and released upon heating or cooling. Optionally, the soft material layer 1010 is made of a safe and comfortable material to reduce skin irritation. Optionally the pad 1008 is made of a dishwasher- and/or washer-safe material for repeated use. Optionally, the pad 1008 is disposable. Optionally, the pad can be heated or cooled prior to insertion into the system. In one embodiment, the system does not contain a power supply or heating element and the pads, which can be removable, reusable or disposable, can be heated (e.g., by microwave) or cooled (e.g., by freezing or refrigeration) prior to use. The pads can contain liquid such as water and/or other agents including oils or medications. Different pads can be used for different purposes (e.g., heating/cooling). The pads may comprise several layers. For example, the pad may have a top layer which is comfortable skin allergy tested, a middle layer that is absorbent, and a bottom layer that is heat/cool resistant and liquid proof. The inner side of the cup may change temperature and heat or cool the pad. The cup and pad is configured to accept breasts or udders. The pad may contain multiple soothing mediums or medications.

FIG. 11 is a schematic of an exemplary portable system and base for maintaining breast health provided herein. The system comprises a removable substrate 1108, with two cups 1102, an on/off switch 1112, a temperature control unit or temperature adjustment assembly 1114, a medium level indicator 1116, and handles 1110. The system comprises a vapor control system including plates and a flow or vapor control switch 1106. A flexible joint 1104 provides communication from the container, through the vapor control system, to the cups 1102. FIG. 11 also shows an optional flat platform 1118 upon which the provided systems can be mounted. The flat platform 1118 optionally comprises a wheel base 1122 that allows the system and platform on top to move freely. The height is adjustable, for example, by knob 1120. Optionally, the cup 1102 can be replaced with multiple cups for use on udders.

Figure 12:
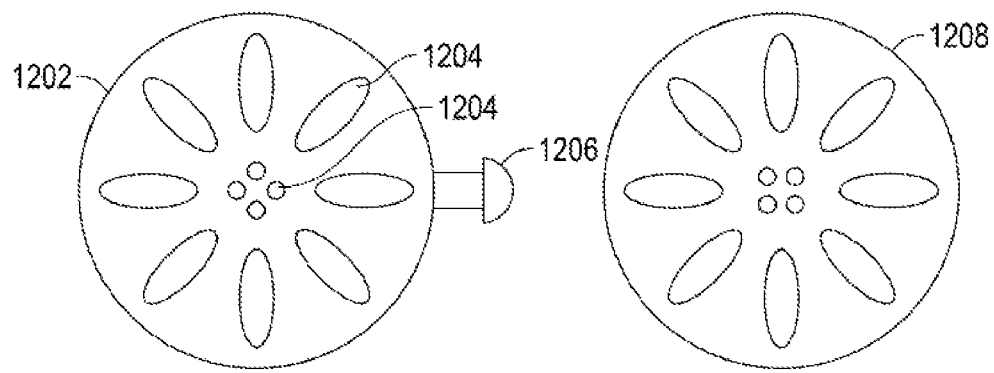
FIG. 12 is a schematic of movable plates for use in the provided systems for maintaining breast health.

FIG. 12 shows an exemplary vapor control system comprising fixed plates 1208 and movable plates 1202 with holes 1204. The movable plate comprises a vapor control switch 1206 to control the flow of vapor from the container to the cups.

FIG. 13 is a schematic of a collapsible cup for use in the provided systems for maintaining breast and udder health with collapsible rings 1302, 1304, and 1306 to adjust for different breast or udder sizes.

Figure 14:
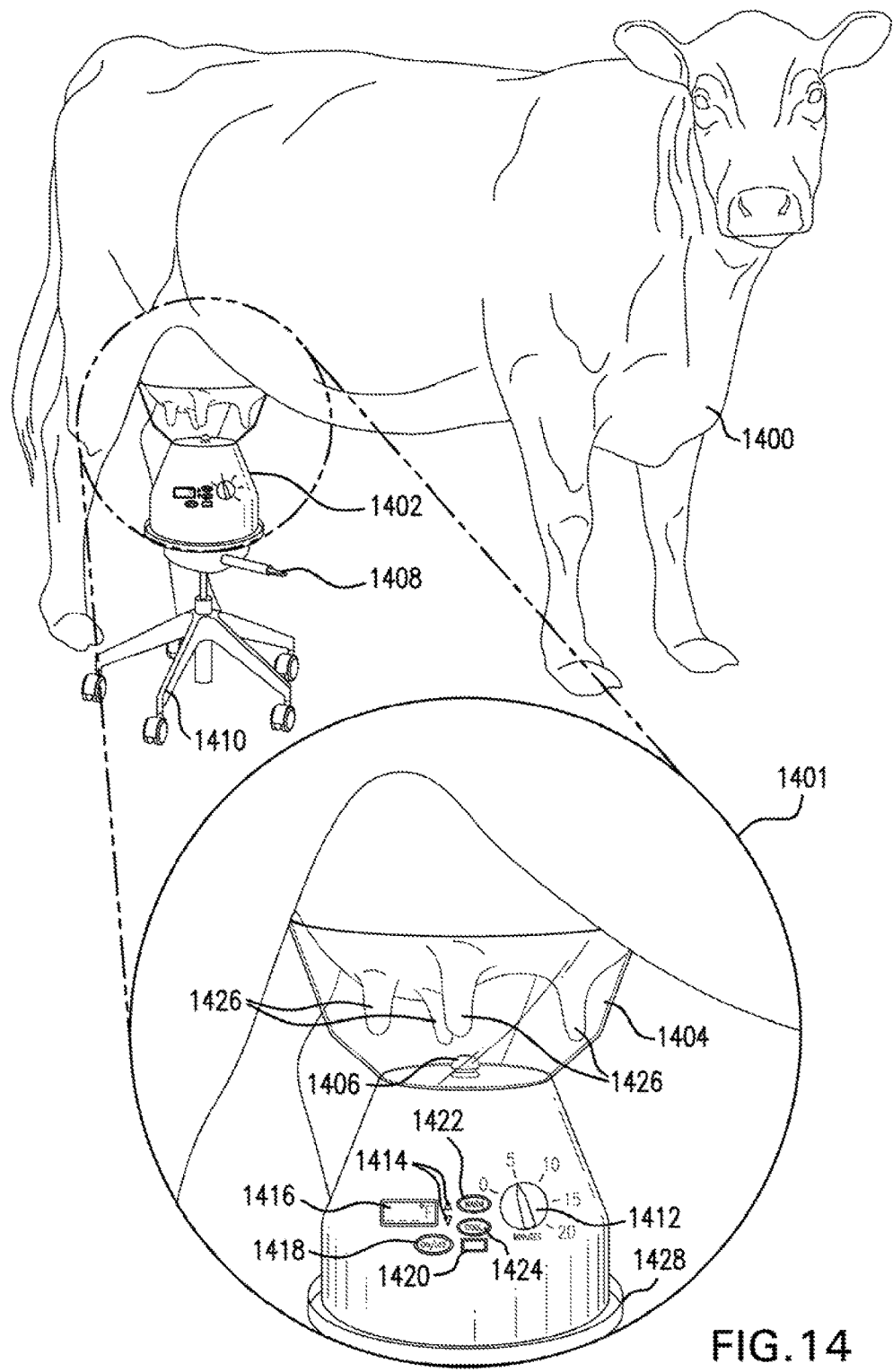
FIG. 14 is a schematic of an exemplary movable system and base for maintaining udder health provided herein.

FIG. 14 is a schematic of an exemplary movable system and base for maintaining udder health of a cow 1400 provided herein with a main body 1402 and a wheel base 1410 that allows the system and platform on top to move freely. The height is adjustable, for example, by knob 1408. A close-up view 1401 of the main body 1402 shows a base 1428 and a cup 1404 that is configured to accept complete or part of the udder. Optionally, four cups can be used cover the four teats 1426 individually. A nozzle 1406 releases substances such as vapors, gases, liquids, or solid particles toward the udder and teats. Optionally, the system comprises a display panel 1416 for displaying temperature, time or other desired properties, a button 1422 for selecting warm therapy, a button 1424 for selecting cool therapy, a timer 1412, a pair of buttons 1414 to adjust temperature, time or other desired properties, and an on/off switch 1418. The system optionally can spray substances through nozzle 1406 by pressing a button 1420. Optionally, the system further comprises a container to collect milk and other secretion and discharge from the udder.

Figure 15:
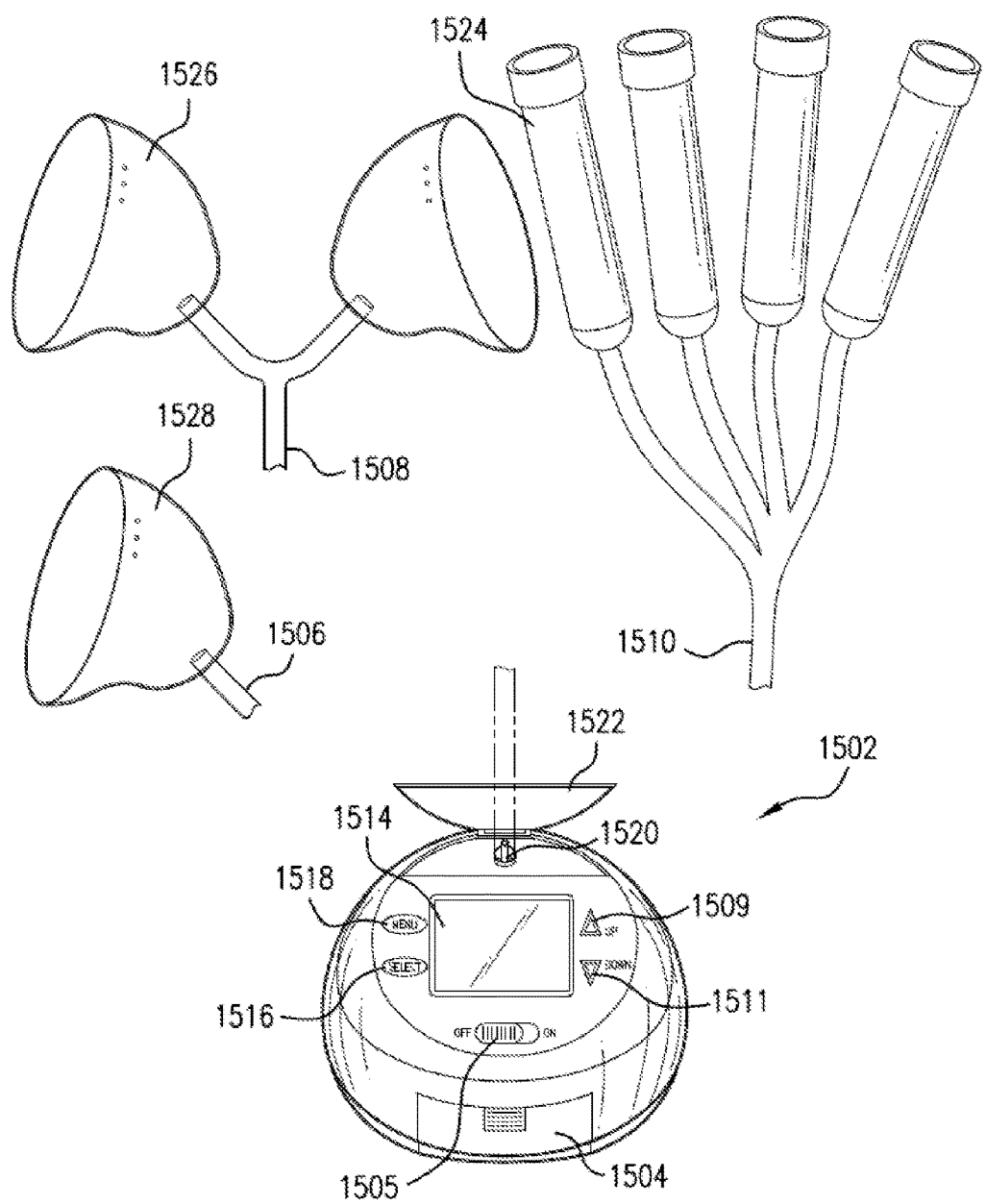
FIG. 15 is a schematic of an exemplary system for maintaining breast and udder health provided herein.

FIG. 15 is a schematic of an exemplary system for maintaining breast and udder health provided herein. The system comprises a main body 1502. The substance is stored in a container 1504. Vapor released from the main body 1502 flows through an opening 1520 into a detachable flexible connector 1506, 1508, or 1510, which guides the vapor to flow from the container to the breast or udder through one (1528) or multiple cups (1526, 1524). When the connectors 1506, 1508, or 1510 are not connected to the main body 1502, the opening 1520 can be covered by a lid 1522. The connectors can have various lengths. An air/vapor pump can be added in the main body 1502 to add enough pressure for the vapor to flow through the connectors into the cup or cups. The system comprises an on/off switch 1505, a menu button 1518, a select button 1516, a display panel 1514 to display the pumping speed, temperature, time, and other properties. A pair of buttons 1509 and 1511 is used to increase or decrease a selected property.

Optionally, the provided systems can be integrated into a breast pump or milk machine. The system may share the same elements that already exist in a breast pump or milk machine including but not limited to the power source, the pump, the cups and the connecting tubes.

Figure 16:
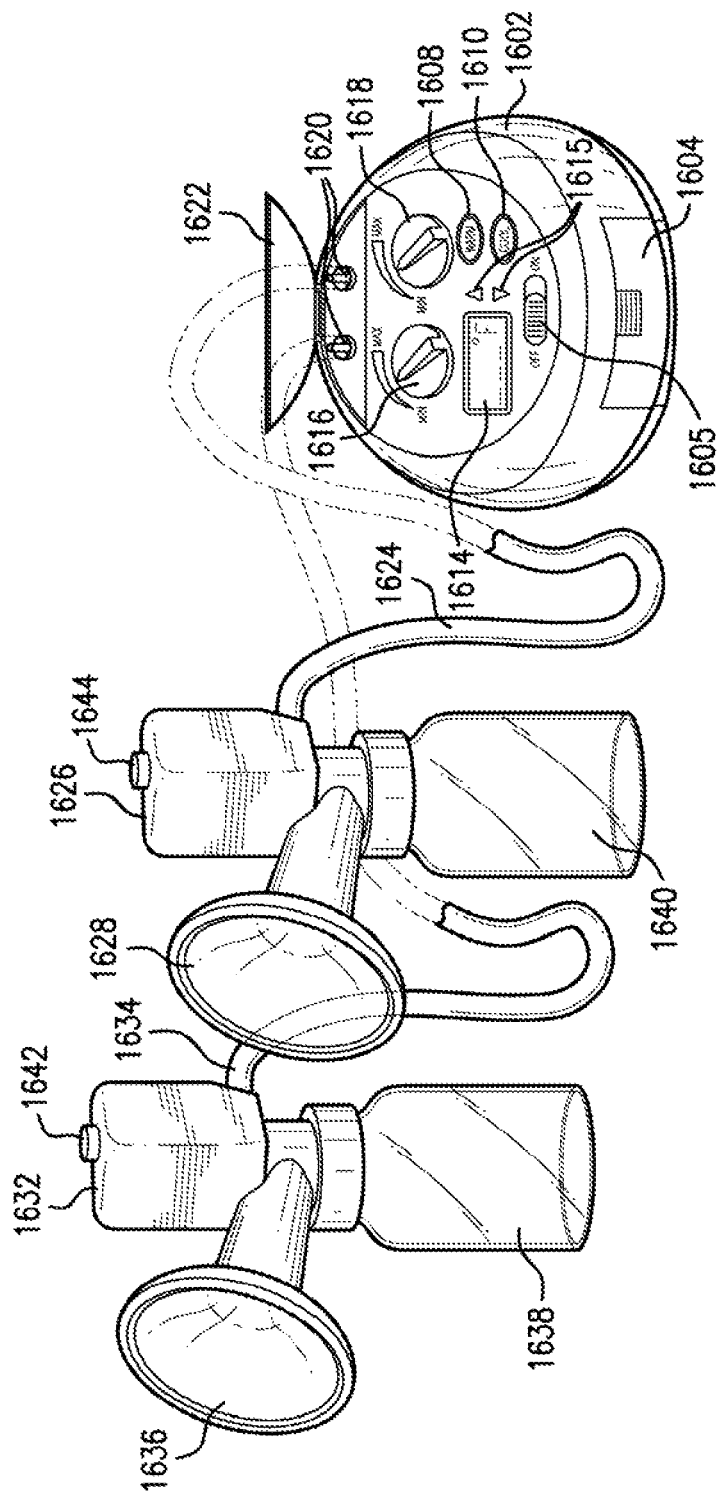
FIG. 16 is a schematic of an exemplary system for maintaining breast and udder health provided herein.

FIG. 16 is a schematic of an exemplary system for maintaining breast health that is integrated into a breast pump provided herein. The system comprises a main body 1602, two detachable flexible connectors 1624 and 1634 and two milk collectors 1638 and 1640. The collectors can be regular milk bottles. When the connectors 1624 and 1634 are removed from container 1602, the nozzles 1620 can be covered by a cap 1622. The substance to be provided to the breast is stored in a container 1604. Optionally, the container is removable, reusable or disposable. The system includes a display panel 1614 for displaying temperature, time or other desired properties, a button 1608 for selecting warm therapy, a button 1610 for selecting cool therapy, a pair of buttons 1615 to adjust temperature, time or other desired properties, and an on/off switch 1605. The vapor/gas release speed and/or pumping speed are controlled by two knobs 1616 and 1618. Vapor and/or gas released from the main body 1602 flows into two nozzles 1620. Two detachable flexible connectors 1624 and 1634 guide the vapor to flow from the nozzles 1620 to the cups 1628 and 1636. The compartments 1626 and 1632 may contain pumps that can spray the breast and nipple with a substance stored within, such as a skin protection agent, antiseptic solution, antibacterial agent, antifungal agent, pain relief medication, and the like. The substance can be in the form of vapor, gas, fine solid or liquid particles. Removable caps 1642 and 1644 can be used to cover the openings for adding substances to the containers 1626 and 1632. Caps 1642 and 1644 can also serve as buttons, that control release of the substances in containers 1626 and 1632.

Similar configurations may be used for integration with milking machines. The vaporizer may have one outlet which is connected to a tube with multiples cups covering the teats. The same pump maybe used to pump in the vapor and pump out the milk. The collection container may be the collection container of the breast pump or milking machine.

Provided herein are systems using warm or cool vapor to maintain breast or udder health. The provided systems can use various media, including hot or cold liquids, e.g., water, or solids, e.g., ice. For example, hot liquid such as hot water from the tap, coffee maker, microwave, hot water kettle or other water heating device can be added to the container to provide warm vapor. Optionally, the system can be microwaved to heat the media. Optionally, the system can be refrigerated or frozen to cool the media.

Optionally, provided portable systems have two separate containers and cups that can be stacked together. The bases of the containers can be mounted upon a base with a connecting element, e.g., an extendible bridge or arm, to fit each user's breasts or multiple teats of the udder by changing the distance between the two separate containers and cups. This design also allows the user to choose only to use one set of the container and application system for one breast or one teat of the udder.

In addition to providing vapor, the provided systems optionally include one or more massaging apparatuses or suctioning apparatuses. Massaging apparatuses for massaging breasts or udders include, for example, vibrators. Massaging can be realized by changing the pressure within a chamber of soft, flexible material inside the cup to massage the breast or udder. Suctioning apparatuses can be used after or during vapor application to collect milk from breasts or udders. Suctioning apparatuses or pumps for use in the provided systems include, but are not limited to, motorized pumps. Motorized pumps are known and described in, for example, U.S. Pat. No. 5,776,098, which is incorporated by reference herein in its entirety. The system optionally further comprises a milk collection container to collect liquid, e.g., milk, from the cups. Collection elements include those described in, for example, U.S. Pat. No. 7,896,835, which is incorporated by reference herein in its entirety. For example, the cup may contain a tube connecting the cup to a milk collection container.

Optionally, the provided systems may be incorporated into bra-like elements. Exemplary bra-like breast pumps are known and are described in U.S. Pat. No. 8,142,393, which is incorporated by reference in its entirety.

Optionally, the provided systems can be integrated into a breast pump or milk machine. Optionally, the container for storing a substance and a heating/cooling element can be integrated into the body of a breast pump or milk machine. If an external power source is used, the system may share the same power source with the breast pump or milk machine.

The vapor can be pumped into tube(s) and delivered to the breasts and udders/teats through cup(s) (such as illustrated in FIGS. 14, 15 and 16). The system may share the elements that already exist in a breast pump or milk machine. For example, the pump used to extract the vapor from the vapor chamber may be the same pump that extracts the milk from the breasts or udders. A switch and/or a valve can be added to the pump to change the direction of the air flow. Cup(s) that deliver the vapor may be the same one(s) used for extracting milk by breast pump and milk machine. The tube(s) that connect the vapor chamber to the cup(s) may be the same ones that connect the cup and the breast pump or milk machine. The collection container may be the collection container is used by the breast pump or milking machine. A switch and/or a valve can be added to control whether or not the tube will be connected to the vapor chamber.

Optionally, the system may be integrated into a hand-held breast pump. A container with the substance at a desired temperature can be integrated to the breast pump. As the subject asserts pressure on the pump, vapor and particles released from the substance can be pumped to the cup.

As stated above, the system can comprise one or more containers in various forms to store one or more types of substances. Optionally, the container comprises a pad or compartment comprising one or more types of substances. The container (including the pad and compartment) can comprise one or more gases, gels, liquids or solids. Optionally, the container comprises one or more liquids, e.g., water or processed water (e.g., purified, distilled or demineralized water). Optionally, the container comprises a gas, liquid, cream, gel, ice, oil, medication, or combinations thereof. Optionally, the container comprises an acid, such as vinegar, an essential oil, a skin conditioning agent, a skin protectant, an antiseptic, an antibiotic, an antifungal agent, an anesthetic agent, or combinations thereof. Optionally, the container comprises a porous element, e.g., a sponge or membrane.

The containers and pads can include lanolin, lanolin oil, or combinations thereof. Lanolin oil may include, lanolin or pure lanolin (lansinoh). Lanolin is a waxy secretion of the ovine sebaceous gland that consists primarily of various esters that include compounds exhibiting a wide range of viscosity from mobile liquids to hard waxes. Lanolin is usually found in hand and nail cream. Lanolin oil is a physical derivative of lanolin and can be used to provide similar benefits as lanolin with a lighter and less viscous composition.

Other oils including essential oils for use in the provided methods and systems include, for example, ester oils and vegetable oils, such as sunflower seed oil, linoleic acid, canola oil, safflower oil, lavender oil, chamomile oil, noni seed oil, corn oil, soy oil, evening primrose oil, pumpkin oil, wheat germ oil, rice bran oil, fractionated coconut oil, caprylic/capric triglycerides, palm kernel oil, or combinations thereof.

Suitable skin conditioning agents that protect dry or damaged skin for use in the provided systems and methods include, but are not limited to, acetyl cysteine, N-acetyl dihydrosphingosine, acrylates/behenyl acrylate/dimethicone acrylate copolymer, adenosine, adenosine cyclic phosphate, adenosine phosphate, adenosine triphosphate, alanine, albumen, algae extract, allantoin and derivatives, *aloe barbadensis* extracts, amyloglucosidase, arbutin, arginine, bromelain, buttermilk powder, butylene glycol, calcium gluconate, carbocysteine, carnosine, beta-carotene, casein, catalase, cephalins, ceramides, *chamomilla recutia* (matricaria) flower extract, cholecalcifoerol, cholesteryl esters, cocobetaine, corn starch modified, crystallins, cyclolethoxymethicone, cysteine DNA, cytochrome C, darutoside, dextran sulfate, dimethicone copolyols, dimethylsilanol hyaluronate, elastin, elastin amino acids, ergocalciferol, ergosterol, fibronectic, folic acid, gelatin, gliadin, beta-glucan, glucose, glycine, glycogen, glycolipids, glycoproteins, glycosaminoglycans, glycosphingolipids, horseradish peroxidase, hydrogenated proteins, hydrolyzed proteins, jojoba oil, keratin, keratin amino acids, kinetin, lactoferrin, lanosterol, lecithin, linoleic acid, linolenic acid, lipase, lysine, lysozyme, malt extract, maltodextrin, melanin, methionine, niacin, niacinamide, oat amino acids, oryzanol, palmitoyl hydrolyzed proteins, pancreatin, papain, polyethylene glycol, pepsin, phospholipids, phytosterols, placental enzymes, placental lipids, pyridoxal 5-phosphate, quercetin, resorcinol acetate, riboflavin, *saccharomyces* lysate extract, silk amino acids, sphingolipids, stearamidopropyl betaine, stearyl palmitate, tocopherol, tocopheryl acetate, tocopheryl linoleate, ubiquinone, *vitis vinifera* (grape) seed oil, wheat amino acids, xanthan gum, zinc gluconate, or combinations thereof.

The container may also include a skin protectant, which may protect injured or exposed skin or mucous membrane surfaces from harmful or irritating external compounds. Suitable skin protectants include, without limitation, algae extract, allantoin, aluminum hydroxide, aluminum sulfate, *camellia sinensis* leaf extract, cerebrosides, dimethicone, glucuronolactone, glycerin, kaolin, lanolin, malt extract, mineral oil, petrolatum, potassium gluconate, talc, or combinations thereof.

The provided containers can comprise one or more active ingredients, such active ingredients may produce both pharmacological and cosmetic effects for varying periods of time and will typically include such active substances as, for example, emollients, humectants, vitamins, hormones, antibiotics, anesthetics, antiseptics, and other therapeutic substances.

Antibiotics include, but are not limited to, penicillin, sodium cloxacillin, cephapirin sodium, cephalexin, tetracycline, ampicillin, tetracyclines, and dicloxacillin.

Antifungal agents include, but are not limited to, clotrimazole, ketoconazole, and miconazole.

Antiseptics include, but are not limited to, alcohols, sodium bicarbonate, sodium chloride, sodium hypochlorite, calcium hypochlorite, polyhexanide, phenol compounds, iodine, and quaternary ammonium compounds.

Emollients include, for example, acetyl arginine, acetylated lanolin, algae extract, apricot kernel oil polyethylene glycol-6 esters, avocado oil, polyethylene glycol-II esters, bis-polyethylene glycol-4 dimethicone, butoxyethyl stearate, C 18 C 36 acid glycol ester, C 12 C 13 alkyl lactate, caprylyl glycol, cetyl esters, cetyllaurate, coconut oil polyethylene glycol-10 esters, di-C 12 C 13 alkyl tartrate, diethyl sebacate, dihydrocholesteryl butyrate, dimethiconol, dimyristyl tartrate, disteareth-5 lauroyl glutamate, ethyl avocadate, ethylhexyl myristate, glyceryl isostearates, glyceryl oleate, hexyldecyl stearate, hexyl isostearate, hydrogenated palm glycerides, hydrogenated soy glycerides, hydrogenated tallow glycerides, isostearyl neopentanoate, isostearyl palmitate, isotridecyl isononanoate, laureth-2 acetate, lauryl polyglyceryl-6 cetearyl glycol ether, methyl gluceth-20 benzoate, mineral oil, myreth-3 palmitate, octyldecanol, octyldodecanol, odontella aurita oil, 2-oleamido-1,3 octadecanediol, palm glycerides, polyethylene glycol avocado glycerides, polyethylene glycol castor oil, polyethylene glycol-22/dodecyl glycol copolymer, polyethylene glycol shea butter glycerides, phytol, raffinose, stearyl citrate, sunflower seed oil glycerides, tocopheryl glucoside, or combinations thereof.

Humectants are ingredients that may help maintain moisture levels in skin. Suitable humectants for use in the provided methods and systems include, for example, acetyl arginine, algae extract, *aloe barbadensis* leaf extract, 2,3-butanediol, chitosan lauroyl glycinate, diglycereth-7 malate, diglycerin, diglycol guanidine succinate, erythritol, fructose, glucose, glycerin, honey, hydrolyzed wheat protein/polyethylene glycol-20 acetate copolymer, hydroxypropyltrimonium hyaluronate, inositol, lactitol, maltitol, maltose, mannitol, mannose, methoxy polyethylene glycol, myristamidobutyl guanidine acetate, polyglyceryl sorbitol, potassium PCA, propylene glycol, sodium PCA, sorbitol, sucrose, urea, or combinations thereof.

The provided containers may comprise an anti-oxidant. Suitable anti-oxidants include, tocopherols and derivatives. Examples of tocopherols and derivates may include, without limitation, vitamin E acetate. Additional examples of anti-oxidants may include vitamin antioxidants and vitamin C and its derivatives.

The provided containers and pads may also comprise various skin care ingredients, including, allantoin, beeswax, castor oil, citric acid, colloidal oatmeal, decyl glucoside, Di-PPG-2 myreth-10 adipate, disodium cocoamphodiacetate, glycerin, green tea extract, jojoba oil, lecithin, meadowfoam oil, olive butter, PEG 150 pentaerythrityl tetrastearate, propylene glycol, diazolidinyl urea, iodopropynyl butylcarbamate, shea butter, silk powder, sodium hydromethylglycinate, sodium PCA, squalane, tapioca starch, or combinations thereof.

The substances above may be present in the container in amounts varying from 0% to 99% by weight of the final composition, particularly from about 0.1% to about 99% by weight of the final composition, and more particularly from about 0.5% to about 50% by weight of the final composition.

Also provided are methods of using the provided systems. Provided are methods and systems for maintaining and improving breast health. For example, the provided systems can provide a substance or substances to breast or udder to prevent and treat causes, symptoms, and conditions of breast/udder diseases. The substance includes but not limited to vapor, gas, particles, or a mixture of any combination of vapor, gas, and particles. For example, the present disclosure provides methods and systems to prepare breasts for breastfeeding or pumping (e.g., to extract milk), to soothe breasts during and/or after breastfeeding or pumping, to prevent or reduce one or more symptoms associated with sore breasts, breast engorgement, plugged duct, breast infection, mastitis, nipple injuries, nipple discharge, or other diseases or conditions resulting in painful or discomfort to breasts or udders. Similarly, also provided are methods and systems to prepare udders for milking, to soothe udders during and/or after milking, to prevent or reduce one or more symptoms associated with clinical or subclinical udder diseases and conditions such as mastitis. As used herein the term milking includes the pumping of udders to extract milk.

Use of the provided systems on breasts and udders may help increase blood circulation. Substances released onto the breasts such as skin protection agents, negative ions, vapors from essential oil and water vapor may help maintain breast health. Use of the provided systems during pregnancy may have the benefit of opening the milk duct, increasing blood circulation, relieving sore breasts, and helping prepare breasts for breastfeeding. Use of the provided systems prior to breast feeding/pumping or milking helps milk flow naturally from the breasts or udders, reduces pumping time and reduces breast injuries. Optionally, the symptom is swelling or pain and the vapor reduces the swelling or pain of the breasts or udder. Provided is a method for preparing breasts for breast feeding or pumping, or udders for milking comprising providing substance (e.g., temperature-controlled) to one or more breasts or udders of a subject. Optionally, the substance is provided directly to a nipple or teat of a subject. Provided is a method for soothing breasts after breast feeding or pumping, soothing udders after milking, or weaning from breastfeeding, comprising providing substance (e.g., temperature-controlled) to one or more breasts or to the udder of a subject. Optionally, the substance cools the one or more breasts or the udder. Optionally, the substance provides moist heat to the one or more breasts or the udder. Optionally, the substance is provided from about 1 to 20 minutes. Optionally, the substance is provided from about 1 to 3 minutes.

Optionally, the temperature of the substance (e.g., vapor) is about −25° C. to 100° C., inclusive. The temperature of the substance can be any range within −25° C. to 100° C. Optionally, the temperature of the substance is about 15° C.

to 90° C., inclusive. Optionally, the temperature of the substance is about −25° C. to 15° C., inclusive. Optionally, the temperature of the substance is about 38° C. to 100° C., inclusive. Optionally, the temperature of the substance is about −4° C. to 8° C., inclusive. Optionally, the temperature of the substance is about −23° C. to −18° C., inclusive, inclusive.

As used herein the terms treatment, treat, or treating refers to a method of reducing the effects of at least one symptom of a disease or condition. Thus, in the disclosed method, treatment can refer to a 10%, 20%, 30%, 40%, 50%, 60%, 70%, 80%, 90%, or 100% reduction in the severity of at least one symptom of an established disease or condition. It is understood that treatment does not necessarily refer to a cure or complete ablation of the disease, condition, or symptoms of the disease or condition. By way of example, treatment of mastitis can include reduction in somatic cell count (SCC) as measured in a milk sample of a subject. Optionally, mastitis is considered to be treated when the SCC is reduced to a level of about 200,000 cells/ml or below in the milk sample of a subject. Optionally, mastitis is considered to be treated when the SCC is reduced to a level of about 100,000 cells/ml or below. Optionally, mastitis is considered to be treated when little to no bacteria is detected in a milk sample of a subject.

As used herein, the terms prevent, preventing, and prevention of a disease or condition refers to an action, for example, administration of a composition, that occurs before or at about the same time a subject begins to show one or more symptoms and conditions of the disease or condition which inhibits or delays onset or severity of one or more symptoms of the disease or condition. As used herein, references to decreasing or reducing include a change of 10%, 20%, 30%, 40%, 50%, 60%, 70%, 80%, 90% or greater as compared to a control level. Such terms can include but do not necessarily include complete elimination. By way of example, mastitis is considered to be prevented when the SCC of a subject remains less than about 200,000 cells/ml as measured in a milk sample of a subject.

As used throughout, applying vapor or substance to breasts or udders includes applying the vapor or substance to the nipple of the breast or to one or more teats of the udder.

Disclosed are materials, compositions, and components that can be used for, can be used in conjunction with, can be used in preparation for, or are products of the disclosed methods and systems. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a system is disclosed and discussed and a number of modifications that can be made to the system are discussed, each and every combination and permutation of the system, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed systems. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

A number of embodiments have been described. Nevertheless, it will be understood that various modifications may be made. Accordingly, other embodiments are within the scope of the claims below.

EXAMPLES

Example 1

Treatment of a Breast Feeding Subject with Mastitis

A subject experiencing recurrent mastitis during the first two months of breast pumping postpartum was treated with vapor at 88° C. for 3 minutes for a period of 7 days prior to each pumping. After the treatment, purified water with antiseptic and skin protection agent were sprayed on the breasts and nipples. Breasts and nipples were air dried or wiped with a sterilized wipe. Prior to treatment, it usually took 15 minutes for the subject to pump all the milk out using a double electric breast pump. After the treatment, it took 7 to 12 minutes to pump all the milk out. Thus, the pumping time was reduced by 20% to 50%. After the 7 day treatment, the subject was treated when breasts were engorged. The subject did not experience a recurrence of mastitis.

Example 2

Treatment of a Breast Feeding Subject with Breast Engorgement

A subject experiencing breast engorgement was treated with vapor at 85° C. for 3 minutes prior to pumping. Milk began secreting from the nipple after 1 to 2 minutes. Prior to treatment, it usually took 10 to 20 minutes for the subject to pump all the milk out using a double electric breast pump. After the treatment, it took 7 to 12 minutes to pump all the milk out.

Example 3

Treatment of Multiple Breast Feeding Subjects with Mastitis

Breast feeding or pumping subjects with mastitis are selected for treatment with the provided systems. Breast feeding or pumping subjects without mastitis are also evaluated as a control. Subjects are treated with vapor at 88° C. for 5 minutes prior to each breast feeding or pumping for the first week. After one week, subjects are treated with vapor at 88° C. for 5 minutes prior to each feeding or pumping and with vapor at 2° C. for 5 minutes after each feeding or pumping. Subjects are evaluated for symptoms associated with mastitis such as bacteria in milk samples. In addition, the breast feeding duration and the volume of milk produced before and after treatment will be compared.

Additional Embodiments

A number of embodiments have been described but a person of skill understands that still other embodiments are encompassed by this disclosure. Non-limiting examples of devices and methods within the scope of the disclosure include below embodiments.

1. A system for maintaining breast health comprising: (a) a first container comprising a top and a bottom, (b) a first cup attached to the top surface of the substrate; (c) a heating element for providing temperature-controlled vapor from the container to the cup; and (d) a cooling element for providing temperature-controlled vapor from the container to the cup.

2. The system of embodiment 1, further comprising a first removable substrate (embodiment 2) covering the top of the container, the removable substrate comprising a top surface and a bottom surface, wherein the removable substrate comprises one or more openings that extend from the top surface of the substrate to the bottom surface of the substrate to allow temperature-controlled vapor to pass from the container to the cup.

3. The system of embodiment 1 or 2, further comprising a valve to control the amount of vapor that passes from the container to the cup.

4. The system of embodiment 3, wherein the valve comprises a vapor control switch capable of opening and closing the valve to control the amount of vapor that passes from the container to the cup.

5. The system of embodiment 2, wherein the removable substrate comprises a fixed plate located between the cup and the openings, the fixed plate comprising one or more holes to allow temperature-controlled vapor to pass from the container to the cup.

6. The system of embodiment 2 or 5, wherein the removable substrate comprises a movable plate located between the cup and the openings, the movable plate comprising one or more holes and a vapor flow control switch to control the amount of vapor that passes from the container to the cup.

7. The system of embodiment 6, wherein the movable plate is located between the fixed plate and the cup.

8. The system of embodiment 6 or 7, wherein the vapor flow control switch facilitates movement of the movable plate.

9. The system of any one of embodiments 6-8, wherein the fixed plate and the movable plate comprise holes of the same size.

10. The system of any one of embodiments 6-9, wherein the fixed plate and movable plate comprise the same number of holes.

11. The system of any one of embodiments 6-10, wherein the flow of vapor is controlled by moving the movable plate using the vapor flow control switch such that the holes in the fixed plate partially or completely overlap the holes on the movable plate.

12. The system of any one of embodiments 6-10, wherein the movable plate can be moved such that none of the holes in the movable plate overlap with the holes in the fixed plate to prevent vapor from flowing from the container to the cup.

13. The system of any one of embodiments 1-12, wherein the cup is removable.

14. The system of any one of embodiments 1-13, wherein the size of the cup is adjustable.

15. The system of any one of embodiments 1-14, wherein the angle of the cup is adjustable.

16. The system of any one of embodiments 1-15, wherein the cup can be collapsed, folded, or expanded.

17. The system of any one of embodiments 1-16, wherein the cup further comprises one or more removable extension rings.

18. The system of any one of embodiments 1-17, wherein the container comprises a substance and an indicator of substance level.

19. The system of embodiment 18, wherein the indicator is a window through which the level of medium is visible.

20. The system of any one of embodiments 1-19, further comprising an insulation layer.

21. The system of any one of embodiments 1-20, further comprising a handle.

22. The system of any one of embodiments 1-21, further comprising a temperature control unit in communication with the heating and cooling elements to control the temperature of the vapor that passes from the container to the cup.

23. The system of any one of embodiments 1-22, further comprising a power source.

24. The system of embodiment 23, wherein the power source is a battery.

25. The system of embodiment 1, wherein the removable substrate comprises a first and second cup attached to the top surface of the substrate.

26. The system of embodiment 1, wherein the system further comprises a second container comprising a top and a bottom, a second removable substrate covering the top of the container, the removable substrate comprising a top surface and a bottom surface, and a second cup attached to the top surface of the second substrate.

27. The system of embodiment 26, wherein the system comprises a connecting element connecting the first and second containers.

28. The system of embodiment 27, wherein the connecting element is an adjustable arm to control the distance between the first and second cups.

29. A system for maintaining breast health comprising
(a) a container comprising a top and a bottom;
(b) a removable substrate covering the top of the container, the removable substrate comprising a top surface and a bottom surface,
(c) two or more cups attached to the top surface of the substrate; and
(d) a temperature-controlling element for providing temperature-controlled vapor from the container to one or more of the cups.

30. The system of embodiment 29, wherein the removable substrate comprises one or more openings that extends from the top surface of the substrate to the bottom surface of the substrate to allow temperature-controlled vapor to pass from the container through the opening to the cups.

31. The system of embodiment 29 or 30, wherein the removable substrate comprises a fixed plate located between the cups and the openings, the fixed plate comprising one or more holes to allow temperature-controlled vapor to pass from the container to the cups.

32. The system of embodiment 30 or 31, wherein the removable substrate comprises a movable plate located between the cup and the openings, the movable plate comprising one or more holes and a vapor flow control switch to control the amount of vapor that passes from the container to the cups.

33. The system of embodiment 32, wherein the flow of vapor is controlled by moving the movable plate using the vapor flow control switch such that the holes in the fixed plate partially or completely overlap the holes on the movable plate.

34. The system of embodiment 32, wherein the movable plate can be moved such that none of the holes in the movable plate overlap with the holes in the fixed plate to prevent vapor from flowing from the container to the cups.

35. The system of embodiment 29 or 30, wherein the system further comprises a valve to control the amount of vapor that passes from the container to the cups.

36. The system of embodiment 35, wherein the valve covers the one or more openings in the removable substrate.

37. The system of embodiment 35, further comprising a vapor control switch capable of opening and closing the valve to control the amount of vapor that passes from the container to the cups.

38. The system of any one of embodiments 29-37, wherein the cups are removable.

39. The system of any one of embodiments 29-38, wherein the size of the cups is adjustable.

40. The system of any one of embodiments 29-39, wherein the angle of the cups is adjustable.

41. The system of any one of embodiments 29-40, wherein the cups can be collapsed, folded, or expanded.

42. The system of any one of embodiments 29-41, wherein the container comprises a substance and an indicator of substance level.

43. The system of embodiment 42, wherein the indicator is a window through which the level of substance is visible.

44. The system of any one of embodiments 29-43, wherein the temperature-controlling element is a heating element.

45. The system of embodiment 44, further comprising an insulation layer.

46. The system of any one of embodiments 29-45, further comprising a second temperature controlling element, the second temperature-controlling element comprises a cooling elements.

47. The system of any one of embodiments 29-46, wherein the container further comprises a handle.

48. The system of any one of embodiments 29-47, further comprising one or more temperature control units.

49. The system of any one of embodiments 29-48, further comprising one or more power sources.

50. The system of embodiment 49, wherein the power source is a battery.

51. The system of any one of embodiments 29-50, further comprising a platform, the container being mounted on top of the platform.

52. The system of embodiment 51, wherein the platform comprises an assembly to adjust the height of the platform.

53. The system of embodiment 51 or 52, wherein the platform is mobile.

54. A system for maintaining breast health comprising an attachment for a breast pump or milking machine comprising
(a) a first container comprising a top portion and a bottom portion,
(b) a first removable substrate covering the top of the container, the removable substrate comprising a top surface and a bottom surface,
(c) a first cup attached to the top surface of the substrate;
(d) a first connector between the cup and the top portion of the first container; and
(e) a second connector for attachment to a breast pump or milking machine.

55. The system of any one of embodiments 1-54, wherein the container comprises one or more liquids.

56. The system of any one of embodiments 1-54, wherein the system comprises an anti-spill element.

57. The system of any one of embodiments 1-56, wherein the container comprises a removable pad.

58. The system of embodiment 57, wherein the removable pad comprises one or more soothing media.

59. The system of any one of embodiments 1-58, wherein the container comprises a skin conditioning agent or a skin protectant.

60. The system of any one of embodiments 1-54, wherein the system further comprises a nozzle for spraying substances onto the breasts.

61. The system of any one of embodiments 1-54, wherein the container comprises water, a gel, ice, an oil, or a medication.

62. The system of any one of embodiments 1-54, wherein the container comprises a porous element.

63. The system of embodiment 62, wherein the porous element is a membrane.

64. The system of any one of embodiments 1-54, wherein the container comprises a liquid and the container further comprises a stirring apparatus.

65. The system of embodiment 64, wherein the stirring apparatus is a bar, a paddle or a fan.

66. The system of embodiment 64, wherein the stirring apparatus is a magnetic stir bar.

67. The system of any one of embodiments 1-54, further comprising a vaporizing element, an ionizer, a device that controls droplet size, or a spray pump.

68. The system of embodiment 67, wherein the vaporizing element is a fan or pump.

69. The system of any one of embodiments 1-68, wherein the system further comprises one or more massaging apparatuses.

70. The system of embodiment 69, wherein the massaging apparatus is a vibrator.

71. The system of any one of embodiments 1-70, wherein the system further comprises a suctioning apparatus.

72. The system of embodiment 71, wherein the system further comprises a collection container to collect liquid from the cups.

73. The system of embodiment 72, wherein the cup comprises a tube connecting the cup to the collection container.

74. The system of embodiment 72, wherein the liquid is milk.

75. The system of any one of embodiments 1-74, wherein the container comprises multiple compartments.

76. A system for maintaining breast health comprising a container comprising a top portion and a bottom portion forming a first cup with a base, wherein the top portion comprises an expanded opening configured for surrounding a breast or udder, wherein the opening is on a plane at an angle with the base of the bottom, wherein the angle of the opening is less than about 90 degrees and more than about 45 degrees as compared to the base of the bottom.

77. The system of embodiment 76, wherein the first cup is configured for holding a vapor producing media or a heating element.

78. The system of embodiment 76, wherein the top portion further comprises one or more second openings on an upper surface of the top portion.

79. The system of embodiment 76, wherein the bottom portion comprises a second cup for collecting milk from a breast or udder.

80. The system of embodiment 76, wherein the system comprises a material suitable for heating and cooling.

81. The system of any one of embodiments 1-80, wherein the system is integrated into a breast pump or milking machine.

82. A method for maintaining breast health in a subject comprising providing vapor to one or more breasts of the subject using the system of any one of embodiments 1-81.

83. A method for preparing breasts for breast feeding or pumping comprising providing temperature-controlled vapor to one or more breasts of a subject using the system of any one of embodiments 1-81.

84. A method for soothing breasts after breast feeding or pumping comprising providing temperature-controlled vapor to one or more breasts of a subject using the system of any one of embodiments 1-81.

85. A method for treating or preventing one or more symptoms associated with breast or udder diseases in a subject comprising providing temperature-controlled vapor to the subject using the system of any one of embodiments 1-81.

86. The method of embodiment 85, wherein the breast disease is breast infection, wherein the breast infection is a bacterial infection or a fungal infection.

87. A method for treating or preventing one or more symptoms associated with breast engorgement in a subject comprising providing temperature-controlled vapor to the subject using the system of any one of embodiments 1-81.

88. The method of any one of embodiments 82-87, wherein the vapor provides moist heat to the one or more breasts.

89. The method of any one of embodiments 82-87, wherein the vapor cools the one or more breasts.

90. The method of any one of embodiments 82-87, wherein the vapor is provided from about 1 to 20 minutes.

91. The method of embodiment 90, wherein the vapor is provided from about 1 to 3 minutes.

What is claimed is:

1. A system for maintaining breast or udder health, comprising a container-section comprising a top portion and a bottom portion, wherein the top portion comprises a receptacle-section receiving one or more breast or udder including the nipple or teat area where milk ducts congregate, wherein the bottom portion comprises a base holding one or more substances that can produce one or more gases, wherein the one or more substances or gases can reach and directly contact the breast or udder area including the nipple or teat area through the receptacle-section, wherein the receptacle-section is on a plane at a fixed or adjustable angle with the base of the bottom portion, wherein the angle of the receptacle-section is equal to or less than approximately 90 degrees and equal to or more than approximately 15 degrees as compared to the base of the bottom portion.

2. The system of claim 1, further comprising a temperature-controlling element to convert the substance to gas, to heat or cool the gas to a desired temperature, or both.

3. The system of claim 1, wherein the substance is at a desired temperature that warms the breast and udder to open milk duct or cools the breast and udder to contract or close milk duct.

4. The system of claim 1, further comprising a collection container for collecting milk from the breast or udder, and wherein the collection container is integrally or removably attached to the system.

5. The system of claim 1, further comprising a component for controlling gas flow from the container-section to the receptacle-section.

6. The system of claim 1, wherein the receptacle-section is removably attached to the container-section.

7. The system of claim 1, further comprising an insulation component configured to maintain temperature within to conserve energy and protect the user.

8. The system of claim 1, further comprising a suctioning apparatus to facilitate collecting milk from the breast or udder.

9. The device of claim 1, wherein the receptacle-section comprises at least one receptacle, wherein each receptacle is configured to receive at least one breast or teat.

10. The system of claim 1, wherein the receptacle-section comprises a removable pad, which optionally contains a media and which can optionally be heated or cooled.

11. A system for maintaining breast or udder health, comprising:
   a. a receptacle-section receiving one or more breast or udder including the nipple or teat area where milk ducts congregate,
   b. a container-section holding one or more substances that can produce one or more gases, wherein the one or more substances or gases can reach and directly contact the breast or udder area including the nipple or teat area through the receptacle-section, wherein the container-section comprises a top portion and a bottom portion,
   c. a heating element, a cooling element or both for providing temperature-controlled gas from the container-section to the receptacle-section.

12. The system of claim 11, further comprising a nozzle through which at least one substance may be sprayed onto the breast or udder.

13. The system of claim 11, wherein the system is integrally or removably associated with a breast pump or milking machine such that milk may flow through the system into a collection container for collecting milk associated with the breast pump or milking machine.

14. The system of claim 11, wherein the container-section is a replaceable container which can be reversibly detached from the receptacle-section.

15. The system of claim 11, further comprising at least one of: a vaporizing element, an ionizer, a device that controls droplet size, or a spray pump.

16. The system of claim 11, further comprising one or more massaging apparatuses.

17. The system of claim 11, further comprising one or more removable collection containers for collecting milk which may flow into the receptacle-section.

18. A method of maintaining breast and udder health using a system, comprising a container-section comprising a top portion and a bottom portion, wherein the top portion comprises a receptacle-section receiving one or more breast or udder including the nipple or teat area where milk ducts congregate, wherein the bottom portion comprises a base holding one or more substances that can produce one or more gases, wherein the one or more substances or gases can reach and directly contact the breast or udder area including the nipple or teat area through the receptacle-section, wherein the receptacle-section is on a plane at a fixed or adjustable angle with the base of the bottom portion, wherein the angle of the receptacle-section is equal to or less than approximately 90 degrees and equal to or more than approximately 15 degrees as compared to the base of the bottom portion,
   comprising the steps of:
   a. directing a gas at a desired temperature which assists milking or feeding to a breast or udder by placing a receptacle-section around at least a portion of the breast or udder including the nipple or teat area to warm the breast and udder to open milk duct; and
   b. feeding directly or pumping with a breast ump or milking machine to empty the breast and udder; and, optionally, c. directing a gas at a desired temperature to the breast or udder through the receptacle-section of the system to cool the breast or udder to contract or close milk duct after feeding or pumping.

19. The system of claim 1, further comprising a protection component configured to alleviate or prevent one or more substance in non-gaseous form from entering the receptacle-section.

20. The device of claim 1, further comprising an apparatus to generate and or assist in the dispersion of gas generated by one or more substances in the container-section.

21. A method of maintaining breast and udder health using a system, comprising:
 a. a receptacle-section receiving one or more breast or udder including the nipple or teat area where milk ducts congregate,
 b. a container-section holding one or more substances that can produce one or more gases, wherein the one or more substances or gases can reach and directly contact the breast or udder area including the nipple or teat area through the receptacle-section, wherein the container-section comprises a top portion and a bottom portion,
 c. a heating element, a cooling element or both for providing temperature-controlled gas from the container-section to the receptacle-section, comprising the steps of:
 a. directing a gas at a desired temperature which assists milking or feeding to a breast or udder by placing a receptacle-section around at least a portion of the breast or udder including the nipple or teat area to warm the breast and udder to open milk duct; and
 b. feeding directly or pumping with a breast pump or milking machine to empty the breast and udder; and, optionally,
 c. directing a gas at a desired temperature to the breast or udder through the receptacle-section of the system to cool the breast or udder to contract or close milk duct after feeding or pumping.

\* \* \* \* \*